(12) United States Patent
Chen et al.

(10) Patent No.: US 8,389,734 B2
(45) Date of Patent: *Mar. 5, 2013

(54) AMIDES USEFUL AS INHIBITORS OF VOLTAGE-GATED SODIUM CHANNELS

(75) Inventors: Weichuan Caroline Chen, San Diego, CA (US); Paul Krenitsky, San Diego, CA (US); Andreas Termin, Encinitas, CA (US); Dean Wilson, Bedford, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 680 days.

This patent is subject to a terminal disclaimer.

(21) Appl. No.: 12/249,251

(22) Filed: Oct. 10, 2008

(65) Prior Publication Data

US 2009/0118333 A1 May 7, 2009

Related U.S. Application Data

(60) Provisional application No. 60/979,292, filed on Oct. 11, 2007.

(51) Int. Cl.
*C07D 251/00* (2006.01)
*C07D 239/00* (2006.01)
*C07D 241/00* (2006.01)
*C07D 213/72* (2006.01)
*A61K 31/53* (2006.01)
*A61K 31/497* (2006.01)
*A61K 31/435* (2006.01)

(52) U.S. Cl. ........ 546/304; 544/180; 544/242; 544/336; 514/241; 514/242; 514/252.1; 514/277

(58) Field of Classification Search .................. None
See application file for complete search history.

(56) References Cited

U.S. PATENT DOCUMENTS

| 3,017,412 A | 1/1962 | Daglish et al. |
| 4,288,449 A | 9/1981 | Bliesener et al. |
| 6,620,849 B2 | 9/2003 | Beaudoin et al. |

FOREIGN PATENT DOCUMENTS

| WO | 02066470 A1 | 8/2002 |
| WO | 02068406 | 9/2002 |
| WO | 03037274 A2 | 5/2003 |
| WO | 2004055006 A1 | 7/2004 |
| WO | 2004106324 A1 | 12/2004 |
| WO | 2005/013914 | 2/2005 |
| WO | 2006053227 A2 | 5/2006 |
| WO | 2007041634 A1 | 4/2007 |

OTHER PUBLICATIONS

Silverman, R. "The Organic Chemistry of Drug Design and Drug Action," 2004, Elsevier, pp. 29-32.*
Neilsen et al. "2-(4-Methoxyphenoxy)-5-nitro-N-(4-sulfamoylphenyl)benzamide activates Kr6.2/SUR1 Katp channels" Biological & Medicinal Chemistry Letters; 14 (2004) 5727-5730.
Nishimori et al. "Carbonic Anhydrase Inhibitors: DNA Cloning and Inhibition Studies of a-Carbonic Anhydrase from Helicobacter pylori, A New Target for Developing Sulfonamide and Sulfamate Gastric Drugs" J. Med. Chem. 2006, 49, 2117-2126.
Scozzafava et al. "Carbonic Anhydrase Inhibitors. Synthesis of Water-Soluble, Topically Effective, Intraocular Pressure-Lowering Aromatic/Heterocyclic Sulfonamides Containing Cationic or Anionic Moieties: Is the Tail More Important than the Ring?" J. Med. Chem. 1999, 42, 2641-2650 XP-002520780.
Supuran et al. "Carbonic anhydrase inhibitors—part 70. Synthesis and ocular pharmacology of a new class of water-soluble, topically effective intraocular pressure lowering agents derived from nicotinic acid and aromatic/heterocyclic sulfonamides" Eur. J. Med. Chem. 34 (1999) 799-808.
International Search Report: PCT/US2008/079544, 2008.

* cited by examiner

*Primary Examiner* — D M Seaman
*Assistant Examiner* — Heidi Reese
(74) *Attorney, Agent, or Firm* — Nancy K. Brennan

(57) ABSTRACT

The present invention relates to compounds useful as inhibitors of voltage-gated sodium channels. The invention also provides pharmaceutically acceptable compositions comprising the compounds of the invention and methods of using the compositions in the treatment of various disorders.

18 Claims, No Drawings

AMIDES USEFUL AS INHIBITORS OF VOLTAGE-GATED SODIUM CHANNELS

CROSS-REFERENCE TO RELATED APPLICATIONS

The present application claims the benefit under 35 U.S.C. §119 of U.S. provisional application Ser. No. 60/979,292, titled "AMIDES USEFUL AS INHIBITORS OF VOLTAGE-GATED SODIUM CHANNELS" filed Oct. 11, 2007, the entire contents of which is hereby incorporated by reference.

TECHNICAL FIELD OF THE INVENTION

The present invention relates to compounds useful as inhibitors of voltage-gated sodium channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See Meisler, M. H., J. A. Kearney, et al. (2002) "Mutations of voltage-gated sodium channels in movement disorders and epilepsy" *Novartis Found Symp* 241: 72-81), multiple sclerosis (See Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73). Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE 1

(Abbreviations: CNS = central nervous system, PNS = peripheral nervous system, DRG = dorsal root ganglion, TG = Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrhythmia, long QT |
| NaV1.6 | CNS widespread, most abundant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L.

(2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV 1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain" *Pain* 83(3): 591-600). The time course of the increase in NaV 1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV 1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir (Wien)* 144(8): 803-10; discussion 810). NaV1.6 and NaV1.7 are also expressed in dorsal root ganglion neurons and contribute to the small TTX sensitive component seen in these cells. NaV 1.7 in particular my therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav 1.1 mutations cause febrile seizures associated with afebrile partial seizures." *Neurology* 57(4): 703-5) and NaV1.2 (See, Sugawara, T., Y. Tsurubuchi, et al. (2001) "A missense mutation of the Na+ channel alpha II subunit gene Na(v) 1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241:189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S, Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1): 11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al, J Neurosci Methods. 2004; 137(2):283-9; neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J. Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol. Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phantom pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; Behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including, urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cyctitis (IC) (see, Giannakopoulos & Campilomatos, Arch Ital Urol Nefrol Androl. 1992; 64(4):337-9; Boucher, M., et al., J Urol. 2000; 164(1):203-8; and prostatitis (see, Mayersak, J. S., Int Surg. 1998; 83(4):347-9; Keith, I. M., et al., J Urol. 2001; 166(1):323-8).

Unfortunately, as described above, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Such undesirable side effects may be avoided by using a Na channel blocker that exhibit a degree of selectivity in its activity against a Na channel subtype. However, Na channel blockers currently in the market lack such selectivity. Perhaps because of this lack of molecular selectivity, drugs currently in the market exhibit use-dependent block and generally show higher affinity at depolarized potentials resulting in the preferential targeting of actively firing neurons, believed to be a key factor in the therapeutic window of existing Na channel blocking drugs. While every drug has it own unique therapeutic profile, current Na channel blockers are generally associated with central nervous system (CNS) and cardiovascular (CV) side-effects, including blood pressure changes, which are often dose-limiting. Dizziness, sedation, nausea, ataxia, and confusion are some of the specific side-effects observed for Phenyloin™, Mexiletine™, and Lidocaine™.

Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

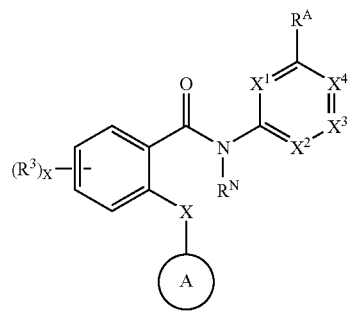

or a pharmaceutically acceptable derivative thereof, wherein $R^3$, $X^1$, $X^2$, $X^3$, $X^4$, $R^N$, X, x and ring A are as defined below.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine and abnormal gastro-intestinal motility.

DETAILED DESCRIPTION OF THE INVENTION

Definitions and General Terminology

The present invention relates to a compound of formula I:

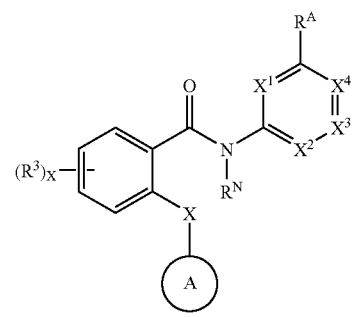

or a pharmaceutically acceptable salt thereof, wherein:
X is O, S, $NR^N$, C(O), or $C(R^N)_2$;
Ring A is phenyl or a 5-7 membered heteroaryl ring, wherein ring A is optionally substituted with up to y occurrences of $R^5$;
$X^1$, $X^2$, $X^3$ and $X^4$ are each independently nitrogen or C—$R^4$ provided that at least one of $X^1$, $X^2$, $X^3$ and $X^4$ is nitrogen and provided that $X^1$, $X^2$, $X^3$ and $X^4$ are not all simultaneously nitrogen;
$R^1$ is selected from $SO_2N(R^2)_2$, $SO_2R^1$, $NR^2SO_2R^1$;
$R^1$ is $C_{1-6}$ aliphatic, wherein up to two carbon atoms other than the atom attached to the nitrogen or oxygen atom is optionally replaced with O, S, $NR^N$, or C(O);
each $R^2$ is independently hydrogen, or $C_{1-6}$ aliphatic, wherein up to two carbon atoms other than the atom attached to the nitrogen or oxygen atom is optionally replaced with O, S, $NR^N$, or C(O);
x is 0-4;
y is 0-4;
each occurrence of $R^N$ is independently selected from hydrogen or a $C_{1-6}$ aliphatic group optionally substituted with 1-3 independent occurrences of —$R^J$, oxo, thioxo, —$CO_2R^J$, —$OR^J$, —$N(R^J)_2$, —$SR^J$, —$NO_2$, halogen, —CN, —$C_{1-4}$haloalkyl, —$C_{1-4}$haloalkoxy, —C(O)N($R^J)_2$, —$NR^JC(O)R^J$, —$SO_2R^J$, —$SO_2N(R^J)_2$, —$NR^JSO_2R^J$, —$NR^JCON(R^J)_2$, —$NR^JCO_2R^J$, —$COR^J$, —$OCOR^J$, —$OCON(R^J)_2$, —$SOR^J$, —$NR^JSO_2N(R^J)_2$, —$COCOR^J$, —$COCH_2COR^J$, —$OP(O)(OR^J)_2$, —$P(O)(OR^J)_2$, —$PO(OR^J)(R^J)$, —$P(O)(R^J)_2$, or —$OP(O)(R^J)_2$; wherein
$R^J$ is hydrogen or unsubstituted $C_{1-6}$ aliphatic;
each occurrence of $R^3$, $R^4$, and $R^5$ is independently Q-$R^X$;
Q is a bond or is a $C_{1-6}$ aliphatic chain wherein up to three methylene units of Q are optionally and independently replaced by —NH—, —NR—, —O—, —S—, —CO$_2$—, —OC(O)—, —C(O)CO—, —C(O)—, —C(S)—, —C(O)NH—, —C(O)NR—, —C(=N—CN)—, —NHCO—, —NRCO—, —NHC(O)O—, —NRC(O)O—, —SO$_2$NH—, —SO$_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO— or —SO$_2$—; wherein Q is optionally substituted with 1-3 independent occurrences of $R^Q$;

each occurrence of $R^X$ is independently selected from —R', halogen, —NO$_2$, —CN, —OR', —SR', —N(R')$_2$, —NR'C(O)R', —NR'C(O)N(R')$_2$, —NR'CO$_2$R', —C(O)R', —CO$_2$R', —OC(O)R', —C(O)N(R')$_2$, —OC(O)N(R')$_2$, —SOR', —SO$_2$R', —SO$_2$N(R')$_2$, —NR'SO$_2$R', —NR'SO$_2$N(R')$_2$, —C(O)C(O)R', —C(O)CH$_2$C(O)R', —OP(O)(OR)$_2$, —P(O)(OR)$_2$, —PO(OR)(R'), —P(O)(R')$_2$, or —OP(O)(R')$_2$;

each occurrence of R is independently selected from hydrogen or a C$_{1-6}$ aliphatic group optionally substituted with 1-3 independent occurrences of —R$^T$, -T-Ar$^1$, halogen, oxo, thioxo, —OR$^T$, —SR$^T$, —N(R$^T$)$_2$, —NO$_2$, —C$_{1-4}$haloalkyl, —C$_{1-4}$haloalkoxy, —CN, —CO$_2$R$^T$, —COR$^T$, —CON(R$^T$)$_2$, —OCOR$^T$, —NR$^T$COR$^T$, —SO$_2$R$^T$, —SO$_2$N(R$^T$)$_2$, or —NR$^T$SO$_2$R$^T$; wherein each R$^T$ is independently hydrogen or unsubstituted C$_{1-6}$ aliphatic; or any two R$^T$ groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of —R$^R$, -T-Ar$^1$, halogen, oxo, thioxo, —OR$^R$, —SR$^R$, —N(R$^R$)$_2$, —NO$_2$, —C$_{1-4}$haloalkyl, —C$_{1-4}$haloalkoxy, —CN, —CO$_2$R$^R$, —COR$^R$, —CON(R$^R$)$_2$, —OCOR$^R$, —NR$^R$COR$^R$, —SO$_2$R$^R$, —SO$_2$N(R$^R$)$_2$, or —NR$^R$SO$_2$R$^R$; wherein each R$^R$ is independently hydrogen or unsubstituted C$_{1-6}$ aliphatic;

T is (CH$_2$)$_w$;

w is 0-2;

Ar$^1$ is selected from a 3-8 membered saturated or partially unsaturated ring, a 5-6 membered aryl ring, a 3-7 membered heterocyclic ring having 1-3 heteroatoms independently selected from nitrogen, oxygen, or sulfur, a 5-6 membered heteroaryl ring having 1-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein Ar$^1$ is optionally substituted with 1-3 independent occurrences of —R$^W$, oxo, thioxo, —CO$_2$R$^W$, —OR$^W$, —N(R$^W$)$_2$, —SR$^W$, —NO$_2$, halogen, —CN, —C$_{1-4}$haloalkyl, —C$_{1-4}$haloalkoxy, —C(O)N(R$^W$)$_2$, —NR$^W$C(O)R$^W$, —SO$_2$R$^W$, —SO$_2$N(R$^W$)$_2$, —NR$^W$SO$_2$R$^W$, —NR$^W$CON(R$^W$)$_2$, —NR$^W$CO$_2$R$^W$, —COR$^W$, —OCOR$^W$, —OCON(R$^W$)$_2$, —SOR$^W$, —NR$^W$SO$_2$N(R$^W$)$_2$, —COCOR$^W$, —COCH$_2$COR$^W$, —OP(O)(OR$^W$)$_2$, —P(O)(OR$^W$)$_2$, —PO(OR$^W$)(R$^W$), —P(O)(R$^W$)$_2$, or —OP(O)(R$^W$)$_2$; wherein R$^W$ is hydrogen or unsubstituted C$_{1-6}$ aliphatic;

R$^Q$ is selected from halogen, —R$^S$, —N(R$^S$)$_2$, —SR$^S$, —OR$^S$, C$_{3-10}$ cycloaliphatic, C$_{6-10}$ aryl, 5-10 membered heteroaryl, 5-10 membered heterocyclyl, oxo, thioxo, —C$_{1-4}$haloalkoxy, —C$_{1-4}$haloalkyl, —NO$_2$, —CN, —CF$_3$, —OCF$_3$, —CO$_2$R$^S$, —COR$^S$, —OC(O)R$^S$ or —NR$^S$C(O)R$^S$; wherein R$^S$ is hydrogen or unsubstituted C$_{1-6}$ aliphatic; or any two R$^Q$ or two R$^S$ groups, or any combination of an R$^Q$ group with an R$^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of R$^O$, halogen, oxo, thioxo, —OR$^O$, —SR$^O$, —N(R$^O$)$_2$, —NO$_2$, —C$_{1-4}$haloalkyl, —C$_{1-4}$haloalkoxy, —CN, —CO$_2$R$^O$, —COR$^O$, —CON(R$^O$)$_2$, —OCOR$^O$, —NR$^O$COR$^O$, —SO$_2$R$^O$, —SO$_2$N(R$^O$)$_2$, or —NR$^O$SO$_2$R$^O$; wherein R$^O$ is hydrogen or unsubstituted C$_{1-6}$ aliphatic; and each occurrence of R' is independently selected from hydrogen or a C$_{1-8}$ aliphatic, C$_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; wherein said C$_{1-8}$ aliphatic, C$_{6-10}$ aryl, heteroaryl ring or heterocyclyl ring is optionally substituted with 1-3 independent occurrences of R$^I$, halogen, oxo, thioxo, —OR$^I$, —SR$^I$, —N(R$^I$)$_2$, —NO$_2$, —C$_{1-4}$haloalkyl, —C$_{1-4}$haloalkoxy, —CN, —CO$_2$R$^I$, —COR$^I$, —CONHR$^I$, —OCOR$^I$, —NR$^I$COR$^I$, —SO$_2$R$^I$, —SO$_2$N(R$^I$)$_2$, or —NR$^I$SO$_2$R$^I$; wherein R$^I$ is hydrogen or unsubstituted C$_{1-6}$ aliphatic.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5 th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group. When more than one position in any given structure may be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include, but are not limited to, methyl, ethyl, propyl, butyl, isopropyl, isobutyl, sec-butyl, tert-butyl, n-pentyl, n-heptyl, or 2-ethylhexyl. The terms "alkyl" and the prefix "alk-", as used herein, are inclusive of both straight chain and branched saturated carbon chain.

The term "alkylene", as used herein, represents a saturated divalent straight or branched chain hydrocarbon group and is exemplified by methylene, ethylene, isopropylene and the like. The term "alkylidene," as used herein, represents a divalent straight chain alkyl linking group.

The term "alkenyl", as used herein, refers to an aliphatic carbon group that contains 2-8 (e.g., 2-6 or 2-4) carbon atoms and at least one carbon-carbon double bond. Like an alkyl group, an alkenyl group can be straight or branched. Examples of an alkenyl group include, but are not limited to, allyl, isoprenyl, 2-butenyl, and 2-hexenyl.

The term "alkynyl", as used herein, refers to an aliphatic carbon group that contains 2-8 (e.g., 2-6 or 2-4) carbon atoms and has at least one carbon-carbon triple bond. An alkynyl group can be straight or branched. Examples of an alkynyl group include, but are not limited to, propargyl and butynyl.

The term "cycloaliphatic" (or "carbocycle"), as used herein, refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: tetrahydrofuran-2-yl, tetrahydrofuran-3-yl, tetrahydrothiophen-2-yl, tetrahydrothiophen-3-yl, 2-morpholino, 3-morpholino, 4-morpholino, 2-thiomorpholino, 3-thiomorpholino, 4-thiomorpholino, pyrrolidin-1-yl, pyrrolidin-2-yl, pyrrolidin-3-yl, tetrahydropiperazin-1-yl, tetrahydropiperazin-2-yl, tetrahydropiperazin-3-yl, piperidin-1-yl, piperidin-2-yl, piperidin-3-yl, piperidin-4-yl, pyrazolin-1-yl, pyrazolin-3-yl, pyrazolin-4-yl, pyrazolin-5-yl, thiazolidin-2-yl, thiazolidin-3-yl, thiazolidin-4-yl, thiazolidin-5-yl, imidazolidin-1-yl, imidazolidin-2-yl, imidazolidin-4-yl, imidazolidin-5-yl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom", as used herein, means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" refers to alkyl, alkenyl or alkoxy, as the case may be, substituted with one or more halogen atoms.

The term, a "haloaliphatic" group refers to an aliphatic group substituted with 1-3 halogen. For instance, the term haloalkyl includes the group —$CF_3$.

The term "halogen" or "halo", as used herein, refers to fluorine, chlorine, bromine or iodine.

The term "oxo", as used herein, refers to =O.
The term "thioxo", as used herein, refers to =S.
The term "carbonyl" group refers to —C(O)—.

The term "aryl" used alone or as part of a larger moiety as in "aralkyl", "aralkoxy", or "aryloxyalkyl", refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic and wherein each ring in the system contains 3 to 7 ring members. The bicyclic and tricyclic groups include benzofused 2- to 3-membered carbocyclic rings. For example, a benzofused group includes phenyl fused with two or more $C_{4-8}$ carbocyclic moieties. The term "aryl" may be used interchangeably with the term "aryl ring."

The term a "bicyclic ring system", as used herein, includes 8- to 12- (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms (e.g., N, O, S, or combinations thereof), wherein each ring in the system contains 3 to 7 ring members and that has a single point of attachment to the rest of the molecule. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). The term "heteroaryl" may be used interchangeably with the term "heteroaryl ring" or the term "heteroaromatic."

Without limitation, monocyclic heteroaryl rings include the following: furanyl (e.g., furan-2-yl or furan-3-yl); imidazolyl (e.g., N-imidazolyl, imidazol-2-yl, imidazol-4-yl, or imidazol-5-yl); isoxazolyl (e.g., isoxazol-3-yl, isoxazol-4-yl, isoxazol-5-yl); oxazolyl (e.g., oxazol-2-yl, oxazol-4-yl, or oxazol-5-yl); pyrrolyl (e.g., N-pyrrolyl, pyrrol-2-yl, or pyrrol-3-yl); pyridinyl (e.g., pyrid-2-yl, pyrid-3-yl, or pyrid-4-yl); pyrimidinyl (e.g., pyrimidin-2-yl, pyrimidin-4-yl, or pyrimidin-5-yl); pyridazinyl (e.g., pyridazin-3-yl, pyridazin-4-yl, pyridazin-5-yl, or pyridazin-6-yl); thiazolyl (e.g., thiazol-2-yl, thiazol-4-yl, or thiazol-5-yl); tetrazolyl (e.g., tetrazol-1-yl or tetrazol-5-yl); triazolyl (e.g., 2-triazolyl or 5-triazolyl), thienyl (e.g., thiophen-2-yl or thiophen-3-yl); pyrazolyl (e.g., pyrazol-2-yl, pyrazol-3-yl, or pyrazol-4-yl); isothiazolyl; 1,2,3-oxadiazolyl; 1,2,5-oxadiazolyl; 1,2,4-oxadiazolyl; 1,2,3-triazolyl; 1,2,3-thiadiazolyl; 1,3,4-thiadiazolyl; 1,2,5-thiadiazolyl; pyrazinyl; 1,3,5-triazinyl. Monocyclic heteroaryls are numbered according to standard chemical nomenclature.

Without limitation bicyclic heteroaryls include the following: indolizyl, indolyl, isoindolyl, 3H-indolyl, indolinyl, benzo[b]furyl, benzo[b]thiophenyl, quinolinyl (e.g., 2-quinolinyl, 3-quinolinyl, or 4-quinolinyl), isoquinolinyl (e.g., 1-isoquinolinyl, 3-isoquinolinyl, or 4-isoquinolinyl), indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $R^3$, $R^4$, $R^5$, $R^N$, $R^J$, $R^Q$, $R^X$, R' or $R^W$. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_2$OR°; —S(O)$_2$N(R°)$_2$; —S(O)R°; —NR°S(O)$_2$N(R°)$_2$; —NR°S(O)$_2$R°; —N(OR°)R°; —C(═NH)—N(R°)$_2$; —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, together with the intervening atoms to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(═N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°—, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each independent occurrence of R° is selected from hydrogen, optionally substituted C$_{1-6}$ aliphatic, an unsubstituted 5-8 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic, cycloaliphatic, heteroaliphatic group, or a non-aromatic heterocyclic ring may contain one or more substituents. In some instances two substituents, on the same atom or on different atoms, together with the intervening atoms to which they are bound, form a 5-7 membered saturated, unsaturated, or partially saturated ring containing 0-3 heteroatoms selected from N, O, or S. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHS(O)$_2$ (alkyl), or ═NR*, where each R* is independently selected from hydrogen or an optionally substituted C$_{1-6}$ aliphatic, or two R* on the same nitrogen are taken together with the nitrogen to form a 5-8 membered heterocyclyl or heteroaryl ring having 1-3 heteroatoms independently selected from nitrogen, oxygen, and sulfur. Optional substituents on the aliphatic group of R* are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo (C₁₋₄ aliphatic), wherein each of the foregoing C₁₋₄ aliphatic groups of R* is unsubstituted.

In some embodiments, optional substituents on the nitrogen of a non-aromatic heterocyclic ring include —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(=S)N(R⁺)₂, —C(=NH)—N(R⁺)₂, or —NR⁺S(O)₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R⁺, on the same substituent or different substituents, taken together with the atom(s) to which each R⁺ group is bound, form a phenyl, 5-8-membered heterocyclyl, 5-8-membered heteroaryl, or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —O(halo(C₁₋₄ aliphatic)), or halo(C₁₋₄ aliphatic), wherein each of the foregoing C₁₋₄ aliphatic groups of R⁺ is unsubstituted.

As detailed above, in some embodiments, two independent occurrences of R° (or R⁺, or any other variable similarly defined herein), are taken together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

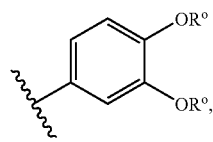

these two occurrences of R° are taken together with the oxygen atoms to which they are bound to form a fused 6-membered oxygen containing ring:

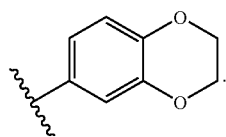 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)₂NR°—, —NR°S(O)₂—, —NR°C(O)NR°—, —OC(O)NR°—, —NR°S(O)₂NR°—, —S(O)—, or —S(O)₂—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH₂CH₂CH₃ was optionally replaced with —O—, the resulting compound could be —OCH₂CH₃, —CH₂OCH₃, or —CH₂CH₂OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

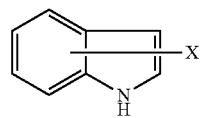

FIG. a

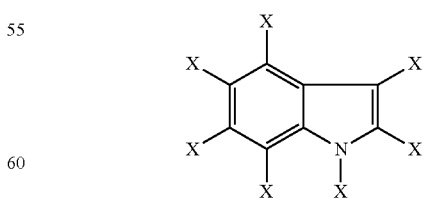

FIG. b

This also applies to multiple ring systems fused to optional ring systems (which would be represented by dotted lines). For example, in Figure c, X is an optional substituent both for ring D and ring E.

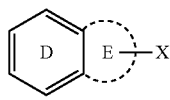

FIG. c

If, however, two rings in a multiple ring system each have different substituents drawn from the center of each ring, then, unless otherwise specified, each substituent only represents substitution on the ring to which it is attached. For example, in Figure d, Y is an optionally substituent for ring D only, and X is an optional substituent for ring E only.

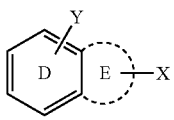

FIG. d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups in Organic Synthesis, 3rd Edition* (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound according to any one of the formulae listed herein. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphorylation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools, probes in biological assays, or sodium channel blockers with improved therapeutic profile.

As used herein, $^1H$ NMR stands for proton nuclear magnetic resonance, and TLC stands for thin layer chromatography.

Description of Compounds of the Invention:

In one embodiment, the present invention provides a compound of formula I:

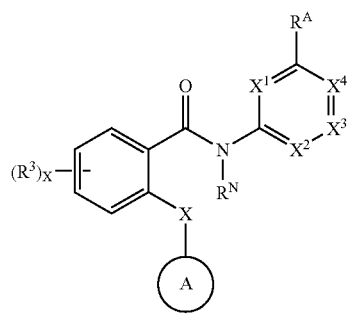

I or a pharmaceutically acceptable salt thereof, wherein:

X is O, S, $NR^N$, C(O), or $C(R^N)_2$;

Ring A is phenyl or a 5-7 membered heteroaryl ring, wherein ring A is optionally substituted with up to y occurrences of $R^5$;

$X^1$, $X^2$, $X^3$ and $X^4$ are each independently nitrogen or C—$R^4$ provided that at least one of $X^1$, $X^2$, $X^3$ and $X^4$ is nitrogen and provided that $X^1$, $X^2$, $X^3$ and $X^4$ are not all simultaneously nitrogen;

$R^4$ is selected from $SO_2N(R^2)_2$, $SO_2R^1$, $NR^2SO_2R^1$;

$R^1$ is $C_{1-6}$ aliphatic, wherein up to two carbon atoms other than the atom attached to the nitrogen or oxygen atom is optionally replaced with O, S, $NR^N$, or C(O);

each $R^2$ is independently hydrogen, or $C_{1-6}$ aliphatic, wherein up to two carbon atoms other than the atom attached to the nitrogen or oxygen atom is optionally replaced with O, S, $NR^N$, or C(O);

x is 0-4;

y is 0-4;

each occurrence of $R^N$ is independently selected from hydrogen or a $C_{1-6}$ aliphatic group optionally substituted with 1-3 independent occurrences of —$R^J$, oxo, thioxo, —$CO_2R^J$, —$OR^J$, —$N(R^J)_2$, —$SR^J$, —$NO_2$, halogen, —CN, —$C_{1-4}$haloalkyl, —$C_{1-4}$haloalkoxy, —C(O)N($R^J$)$_2$, —$NR^JC(O)R^J$, —$SO_2R^J$, —$SO_2N(R^J)_2$, —$NR^JSO_2R^J$, —$NR^JCON(R^J)_2$, —$NR^JCO_2R^J$, —$COR^J$, —$OCOR^J$, —$OCON(R^J)_2$, —$SOR^J$, —$NR^JSO_2N(R^J)_2$, —$COCOR^J$, —$COCH_2COR^J$, —$OP(O)(OR^J)_2$, —$P(O)(OR^J)_2$, —$PO(OR^J)(R^J)$, —$P(O)(R^J)_2$, or —$OP(O)(R^J)_2$; wherein $R^J$ is hydrogen or unsubstituted $C_{1-6}$ aliphatic;

each occurrence of $R^3$, $R^4$, and $R^5$ is independently Q-$R^X$;

Q is a bond or is a $C_{1-6}$ aliphatic chain wherein up to three methylene units of Q are optionally and independently replaced by —NH—, —NR—, —O—, —S—, —$CO_2$—, —OC(O)—, —C(O)CO—, —C(O)—, —C(S)—, —C(O)NH—, —C(O)NR—, —C(=N—CN)—, —NHCO—, —NRCO—, —NHC(O)O—, —NRC(O)O—, —$SO_2$NH—, —$SO_2$NR—, —NHSO$_2$—, —NRSO$_2$—, —NHC(O)NH—, —NRC(O)NH—, —NHC(O)NR—, —NRC(O)NR, —OC(O)NH—, —OC(O)NR—, —NHSO$_2$NH—, —NRSO$_2$NH—, —NHSO$_2$NR—, —NRSO$_2$NR—, —SO— or —$SO_2$—; wherein Q is optionally substituted with 1-3 independent occurrences of $R^Q$;

each occurrence of $R^X$ is independently selected from —R', halogen, —$NO_2$, —CN, —OR', —SR', —N(R')$_2$, —NR'C(O)R', —NR'C(O)N(R')$_2$, —NR'CO$_2$R', —C(O)R', —CO$_2$R', —OC(O)R', —C(O)N(R')$_2$, —OC(O)N(R')$_2$, —SOR', —SO$_2$R', —SO$_2$N(R')$_2$, —NR'SO$_2$R', —NR'SO$_2$N(R')$_2$, —C(O)C(O)R', —C(O)CH$_2$C(O)R', —OP(O)(OR)$_2$, —P(O)(OR)$_2$, —PO(OR)(R'), —P(O)(R')$_2$, or —OP(O)(R')$_2$;

each occurrence of R is independently selected from hydrogen or a $C_{1-6}$ aliphatic group optionally substituted with 1-3 independent occurrences of —$R^T$, -T-$Ar^1$, halogen, oxo, thioxo, —$OR^T$, —$SR^T$, —$N(R^T)_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$; wherein each $R^T$ is independently hydrogen or unsubstituted $C_{1-6}$ aliphatic; or any two $R^T$ groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of —$R^R$, -T-$Ar^1$, halogen, oxo, thioxo, —$OR^R$, —$SR^R$, —$N(R^R)_2$, —$NO_2$, —$C_{1-4}$haloalkyl, —$C_{1-4}$haloalkoxy, —CN, —$CO_2R^R$, —$COR^R$, —$CON(R^R)_2$, —$OCOR^R$, —$NR^RCOR^R$, —$SO_2R^R$, —$SO_2N(R^R)_2$, or —$NR^RSO_2R^R$; wherein each $R^R$ is independently hydrogen or unsubstituted $C_{1-6}$ aliphatic;

T is (CH$_2$)$_w$;

w is 0-2;

$Ar^1$ is selected from a 3-8 membered saturated or partially unsaturated ring, a 5-6 membered aryl ring, a 3-7 membered heterocyclic ring having 1-3 heteroatoms independently selected from nitrogen, oxygen, or sulfur, a 5-6 membered heteroaryl ring having 1-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with 1-3 independent occurrences of —$R^W$, oxo, thioxo, —$CO_2R^W$, —$OR^W$, —$N(R^W)_2$, —$SR^W$, —$NO_2$, halogen, —CN, —$C_{1-4}$haloalkyl, —$C_{1-4}$haloalkoxy, —C(O)N($R^W$)$_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$PO(OR^W)(R^W)$, —$P(O)(R^W)_2$, or —$OP(O)(R^W)_2$; wherein $R^W$ is hydrogen or unsubstituted $C_{1-6}$ aliphatic;

$R^Q$ is selected from halogen, —$R^S$, —$N(R^S)_2$, —SRS, —ORS, $C_{3-10}$ cycloaliphatic, $C_{6-10}$ aryl, 5-10 membered heteroaryl, 5-10 membered heterocyclyl, oxo, thioxo, —$C_{1-4}$haloalkoxy, —$C_{1-4}$haloalkyl, —$NO_2$, —CN, —$CF_3$, —$OCF_3$, —$CO_2R^S$, —$COR^S$, —$OC(O)R^S$ or —$NR^SC(O)R^S$; wherein $R^S$ is hydrogen or unsubstituted $C_{1-6}$ aliphatic; or any two $R^Q$ or two $R^S$ groups, or any combination of an $R^Q$ group with an $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, halogen, oxo, thioxo, —$OR^O$, —SRO, —$N(R^O)_2$, —$NO_2$, —$C_{1-4}$haloalkyl, —$C_{1-4}$haloalkoxy, —CN, —$CO_2R^O$, —$COR^O$, —$CON(R^O)_2$, —$OCOR^O$, —$NR^OCOR^O$, —$SO_2R^O$, —$SO_2N(R^O)_2$, or —$NR^OSO_2R^O$; wherein $R^O$ is hydrogen or unsubstituted $C_{1-6}$ aliphatic; and each occurrence of R' is independently selected from hydrogen or a $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; wherein said $C_{1-8}$ aliphatic, $C_{6-10}$ aryl, heteroaryl ring or heterocyclyl ring is optionally substituted with 1-3 independent occurrences of $R^1$, halogen, oxo, thioxo, —$OR^I$, —$SR^I$, —$N(R^I)_2$, —$NO_2$, —$C_{1-4}$haloalkyl, —$C_{1-4}$haloalkoxy, —CN, —$CO_2R^I$, —$COR^I$, —$CONHR^I$, —$OCOR^I$, —$NR^ICOR^I$, —$SO_2R^I$, —$SO_2N(R^I)_2$, or —$NR^ISO_2R^I$; wherein $R^I$ is hydrogen or unsubstituted $C_{1-6}$ aliphatic.

In some embodiments of compounds of formula I, ring A is optionally substituted phenyl.

In some embodiments of compounds of formula I, ring A is an optionally substituted 5-7 membered heteroaryl ring.

In some embodiments of compounds of formula I, ring A is selected from:
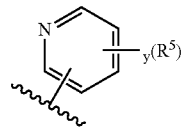 a
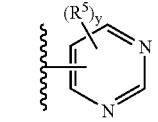 b
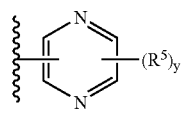 c
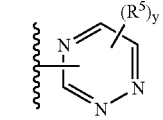 d
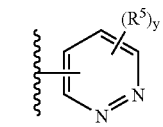 e
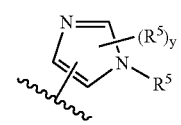 f
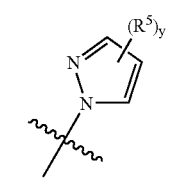 g
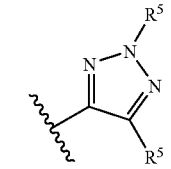 h
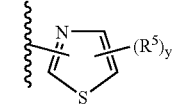 i
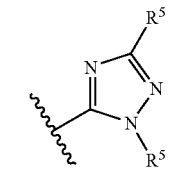 j
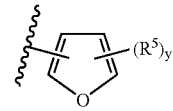 k
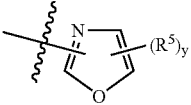 l
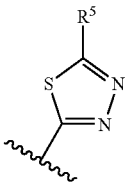 m
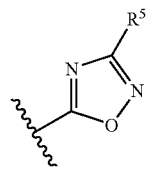 n
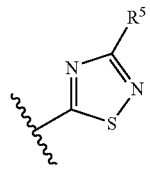 o
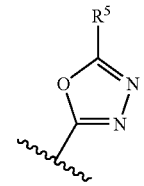 p
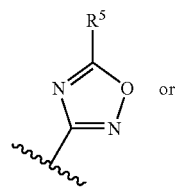 q or
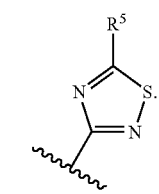 r
In another embodiment of compounds formula I, ring A is:
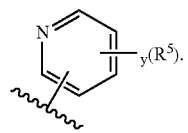

In some embodiments of compounds of formula I, X is O, S, NH, C(O), or CH$_2$.

In other embodiments of compounds of formula I, X is NR$^N$, and R$^N$ is C$_1$-C$_6$ alkyl.

In some embodiments of compounds of formula I, X is C(R$^N$)$_2$, wherein each R$^N$ is independently hydrogen or C$_1$-C$_6$ alkyl.

In other embodiments of compounds of formula I, X is oxygen.

In yet other embodiments of compounds of formula I, X is oxygen and ring A is

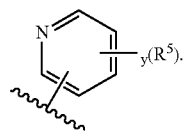

either optionally substituted phenyl or

In some embodiments of compounds of formula I, x is 0-3. In other embodiments, x is 0-2. In yet other embodiments x is 2. In other embodiments, x is 1.

In some embodiments of compounds of formula I, x is 1-3, and each R$^3$ is independently selected from hydrogen, halogen, CN, CF$_3$, NO$_2$, or an optionally substituted group selected from C$_{1-6}$ aliphatic, C$_{1-6}$ cycloaliphatic, C$_{6-10}$ aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NRCOR', —CON(R')$_2$, —S(O)$_2$R', or —S(O)$_2$N(R')$_2$.

In some embodiments of compounds of formula I, x is 1 and R$^3$ is CF$_3$, methyl, ethyl, propyl, isopropyl, t-butyl, or sec-butyl.

In yet other embodiments of compounds of formula I, X is oxygen, ring A is either optionally substituted phenyl or

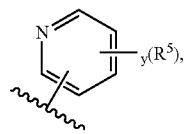

and R$^3$ is CF$_3$ or t-butyl.

In some embodiments of compounds of formula I, radical:

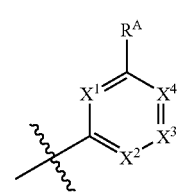

is selected from:

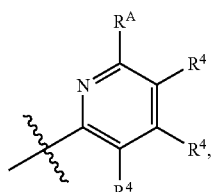  a-1

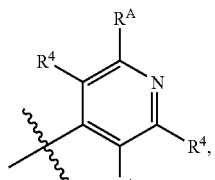  a-2

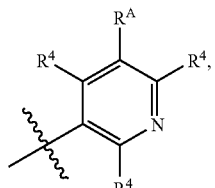  a-3

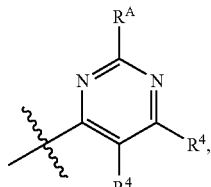  b-1

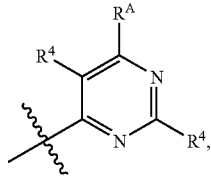  b-2

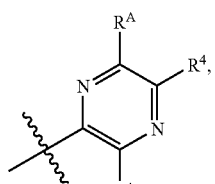  c-1

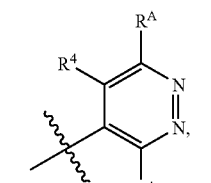  e-1

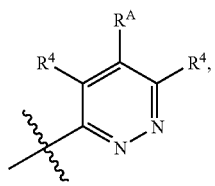  e-2

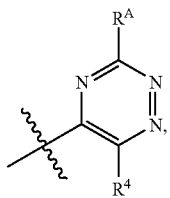
d-1

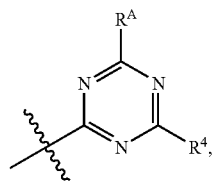
d-2

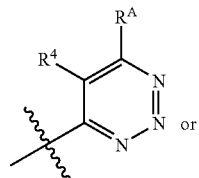
or
d-3

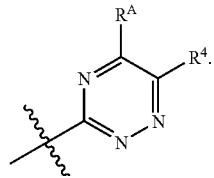
d-5

In some embodiments of compounds of formula I, radical

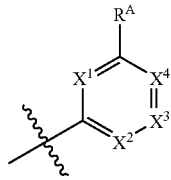

is selected from ring a-1, a-2 or a-3.

In some embodiments of compounds of formula I, ring a-1, a-2, or a-3, each $R^4$ is hydrogen.

In some other embodiments of compounds of formula I, X is oxygen, ring A is either optionally substituted phenyl or

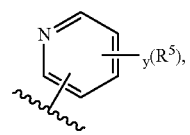

radical

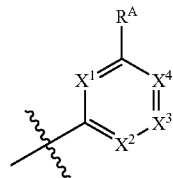

is ring a-3 and $R^3$ is $CF_3$ or t-butyl.

In some embodiments of compounds of formula I, each $R^4$, when present, is independently selected from hydrogen, halogen, CN, $NO_2$, or an optionally substituted group selected from $C_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In other embodiments of compounds of formula I, X is oxygen, ring A is either optionally substituted phenyl or

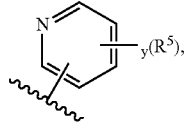

radical

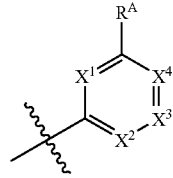

is ring a-3, $R^3$ is $CF_3$ or t-butyl and each $R^4$ is hydrogen.

In some embodiments of compounds of formula I, $R^A$ is selected from $SO_2N(R^2)_2$ or $SO_2R^1$. In other embodiments, $R^1$ is $SO_2N(R^2)_2$ and both $R^2$ are hydrogen. In yet other embodiments, $R^1$ is $SO_2R^1$ and $R^1$ is $C_{1-6}$ alkyl.

In other embodiments of compounds of formula I, X is oxygen, ring A is either optionally substituted phenyl or

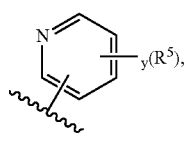

radical

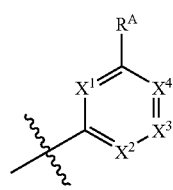

is ring a-3, $R^3$ is $CF_3$ or t-butyl, each $R^4$ is hydrogen and $R^A$ is $SO_2NH_2$ or $SO_2CH_3$.

In some embodiments of compounds of formula I, y is 1-3, and each $R^5$ is independently selected from hydrogen, halogen, CN, NO$_2$, or an optionally substituted group selected from C$_{1-4}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$.

In other embodiments of compounds of formula I, y is 1-3, and each $R^5$ is independently selected from halogen or an optionally substituted C$_{1-4}$ aliphatic group.

In other embodiments of compounds of formula I, y is 1-3, and each $R^5$ is independently selected from fluoro, chloro, CF$_3$, or methyl.

In other embodiments of compounds of formula I, X is oxygen, ring A is either optionally substituted phenyl or

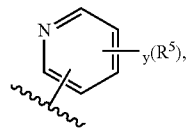

radical

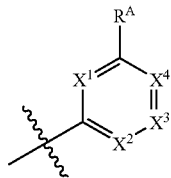

is ring a-3, $R^3$ is CF$_3$ or t-butyl, each $R^4$ is hydrogen, $R^A$ is SO$_2$NH$_2$ or SO$_2$CH$_3$, y is 1 and $R^5$ is selected from methyl, CF$_3$, fluoro or chloro.

In some embodiments of compounds of formula I, $R^N$ is hydrogen.

In other embodiments of compounds of formula I, X is oxygen, ring A is either optionally substituted phenyl or

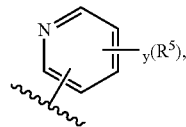

radical

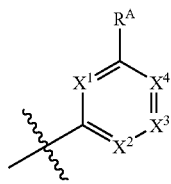

is ring a-3, $R^3$ is CF$_3$ or t-butyl, each $R^4$ is hydrogen, $R^1$ is SO$_2$NH$_2$ or SO$_2$CH$_3$, y is 1, $R^5$ is selected from methyl, CF$_3$, fluoro or chloro and $R^N$ is hydrogen.

In other embodiments of the present invention a compound has the structure of formula I-A:

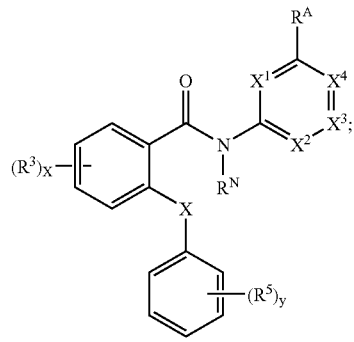

I-A or a pharmaceutically acceptable salt thereof, wherein $X^1$, $X^2$, $X^3$, $X^2$, $R^N$, $R^3$, $R^5$, X, x, and y are as defined herein.

In some embodiments of compounds of formula I-A, X is oxygen.

In some embodiments of compounds of formula I-A, x is 0-3. In other embodiments, x is 0-2. In yet other embodiments, x is 2. In yet further embodiments, x is 1.

In some embodiments of compounds of formula I-A, x is 1-3, and each $R^3$ is independently selected from hydrogen, halogen, CN, CF$_3$, NO$_2$, or an optionally substituted group selected from C$_{1-6}$ aliphatic, C$_{1-6}$ cycloaliphatic, C$_{6-10}$ aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NRCOR', —CON(R')$_2$, —S(O)$_2$R', or —S(O)$_2$N(R')$_2$.

In some embodiments of compounds of formula I-A, x is 1 and $R^3$ is selected from methyl, ethyl, propyl, isopropyl, t-butyl, or sec-butyl.

In some embodiments of compounds of formula I-A, y is 1-3, and each $R^5$ is independently selected from hydrogen, halogen, CN, NO$_2$, or an optionally substituted group selected from C$_{1-4}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —COOR', —NRCOR', —CON(R')$_2$, or —S(O)$_2$N(R')$_2$.

In some embodiments of compounds of formula I-A, y is 1-3, and each $R^5$ is independently selected from Cl, Br, F, CF$_3$, methyl, ethyl, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, piperidinyl, piperazinyl, morpholino, or an optionally substituted group selected from C$_{1-4}$alkoxy, phenyl, phenyloxy, benzyl, or benzyloxy.

In some embodiments of compounds of formula I-A, each $R^4$, when present, is hydrogen.

In some embodiments of compounds of formula I-A, each $R^4$, when present, is independently selected from hydrogen, halogen, CN, NO$_2$, or an optionally substituted group selected from C$_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In some embodiments of compounds of formula I-A, $R^A$ is selected from SO$_2$N(R$^2$)$_2$ or SO$_2$R$^1$.

In other embodiments of compounds of formula I-A, $R^1$ is SO$_2$N(R$^2$)$_2$ and both R$^2$ are hydrogen. In yet other embodiments, $R^A$ is SO$_2$R$^1$ and R$^1$ is C$_{1-6}$ alkyl.

In other embodiments of compounds of formula I-A, X is oxygen, radical

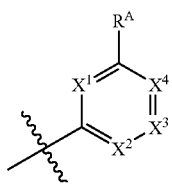

is ring a-3, each $R^4$ is hydrogen, $R^A$ is $SO_2NH_2$ or $SO_2CH_3$, y is 1, $R^5$ is selected from methyl, $CF_3$, fluoro or chloro, $R^N$ is hydrogen and $R^3$ is $CF_3$ or t-butyl.

In other embodiments of the present invention a compound has the structure of formula I-A1, II-A2 or II-A3:

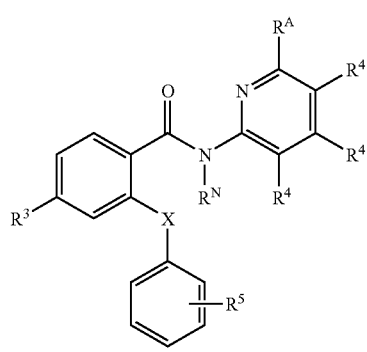

II-A1

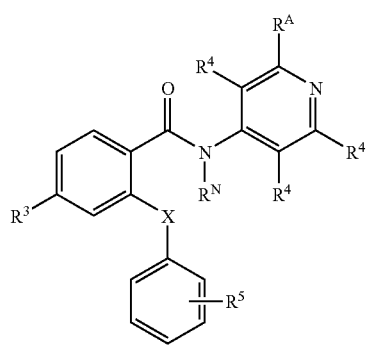

II-A2

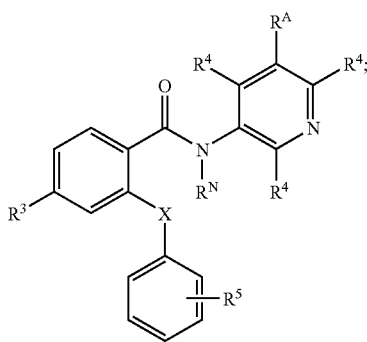

II-A3 or a pharmaceutically acceptable salt thereof, wherein $R^3$, $R^5$, $R^N$, $R^A$, $R^4$ and X are defined herein.

In some embodiments of compounds of formula I-A1, II-A2 or II-A3, $R^3$ is selected from hydrogen, halogen, CN, $NO_2$, or an optionally substituted group selected from $C_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NRCOR', —CON(R')$_2$, or —S(O)$_2$N(R')$_2$.

In some embodiments of compounds of formula II-A1, II-A2 or II-A3, $R^3$ is selected from Cl, Br, F, $CF_3$, methyl, ethyl, isopropyl, t-butyl, isobutyl, CN, —COOH, —N(CH$_3$)$_2$, —N(Et)$_2$, —N(iPr)$_2$, —O(CH$_2$)$_2$OCH$_3$, —CONH$_2$, —COO(C$_{1-6}$ alkyl), —OH, —OCF$_3$, —SCF$_3$, —OCH$_3$, —CH$_2$OH, —NHCOCH$_3$, —SO$_2$NH$_2$, optionally substituted pyrrolyl, thiadiazolyl, pyridyl, imidazolyl, pyrazolyl, piperidinyl, piperazinyl, morpholinyl, or an optionally substituted group selected from $C_{1-4}$alkoxy, phenyl, phenyloxy, benzyl, or benzyloxy.

In some embodiments of compounds of formula II-A1, II-A2 or II-A3, $R^3$ is a $C_1$-$C_6$ alkyl group. In other embodiments, $R^3$ is selected from methyl, ethyl, isopropyl, t-butyl, or sec-butyl.

In some embodiments of compounds of formula II-A1, II-A2 or II-A3, $R^3$ is selected from an optionally substituted pyrrolyl, thiadiazolyl, pyridyl, imidazolyl, pyrazolyl, piperidinyl, piperazinyl, or morpholinyl.

In some embodiments of compounds of formula II-A1, II-A2 or II-A3, $R^5$ is selected from hydrogen, halogen, CN, $NO_2$, or an optionally substituted group selected from $C_{1-4}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —C(O)R', —CH$_2$SR', —COOR', —NRCOR', —CON(R')$_2$, or —S(O)$_2$N(R')$_2$.

In some embodiments of compounds of formula II-A1, II-A2 or II-A3, $R^5$ is selected from Cl, Br, F, $CF_3$, methyl, ethyl, CN, —COOH, —N(CH$_3$)$_2$, —N(Et)$_2$, —N(iPr)$_2$, —O(CH$_2$)$_2$OCH$_3$, —C(O)Me, —CONH$_2$, —COOCH$_3$, —OH, —OMe, —CH$_2$OH, —NHCOCH$_3$, —SO$_2$NH$_2$, methylenedioxy, ethylenedioxy, piperidinyl, piperazinyl, morpholino, or an optionally substituted group selected from $C_{1-4}$alkoxy, phenyl, phenyloxy, benzyl, or benzyloxy.

In some embodiments of compounds of formula II-A1, II-A2 or II-A3, X is oxygen or sulfur; $R^3$ is selected from optionally substituted $C_{1-6}$ aliphatic or $CF_3$; and $R^5$ is selected from CN, $CF_3$, —C(O)R', —COOR', —OR', halogen, optionally substituted $C_{1-4}$ aliphatic, 5-6 membered heteroaryl, or 4-7 membered heterocyclyl.

In some embodiments of compounds of formula II-A1, II-A2 or II-A3, X is oxygen or sulfur; $R^3$ is selected from $CF_3$, methyl, ethyl, propyl, isopropyl, t-butyl, isobutyl or sec-butyl; and $R^5$ is selected from CN, $CF_3$, —C(O)R', —COOR', —OR', —CON(R')$_2$, halogen, optionally substituted $C_{1-4}$ aliphatic, 5-6 membered heteroaryl, or 4-7 membered heterocyclyl.

In yet other embodiments of compounds of formula II-A1, II-A2 or II-A3, X is oxygen; $R^3$ is selected from $CF_3$, methyl, ethyl, propyl, isopropyl, t-butyl, isobutyl or sec-butyl; and $R^5$ is selected from CN, $CF_3$, —C(O)Me, —COOMe, —OMe, F, Cl, Br, ethyl, propyl, isopropyl, t-butyl, isobutyl, sec-butyl, optionally substituted pyridyl, pyrimidinyl, pyrazinyl, pyridazinyl, pyrazinyl, piperidinyl, morpholinyl, piperazinyl, pyrrolidinyl, or azetidinyl.

In some other embodiments of compounds of formula II-A1, II-A2 or II-A3, X is oxygen; $R^3$ is selected from $CF_3$ or t-butyl; and $R^5$ is selected from CN, $CF_3$, —C(O)Me, —COOMe, —OMe, F, Cl, Br, isopropyl, t-butyl, isobutyl, sec-butyl, optionally substituted pyridyl, piperidinyl or morpholinyl.

In some embodiments of compounds of formula I-A1, II-A2 or II-A3, each $R^4$, when present, is hydrogen.

In some other embodiments of compounds of formula I-A1, II-A2 or II-A3, each $R^4$, when present, is independently selected from hydrogen, halogen, CN, $NO_2$, or an optionally substituted group selected from $C_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In some other embodiments of compounds of formula II-A1, II-A2 or II-A3, $R^4$ is selected from SO$_2$N(R$^2$)$_2$ or SO$_2$R$^1$. In yet other embodiments, $R^4$ is SO$_2$N(R$^2$)$_2$ and both R$^2$ are hydrogen. In still other embodiments, $R^4$ is SO$_2$R$^1$ and R$^1$ is C$_{1-6}$ alkyl.

In other embodiments of compounds of formula II-A1, II-A2 or II-A3, X is oxygen, each R$^4$ is hydrogen, R$^1$ is SO$_2$NH$_2$ or SO$_2$CH$_3$, y is 1, R$^5$ is selected from methyl, CF$_3$, fluoro or chloro, R$^N$ is hydrogen and R$^3$ is CF$_3$ or t-butyl.

In other embodiments of the present invention, a compound has the structure of formula III-A, III-B or III-C:

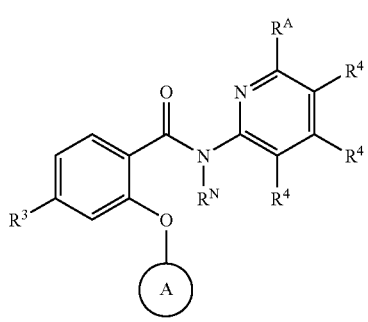

III-A

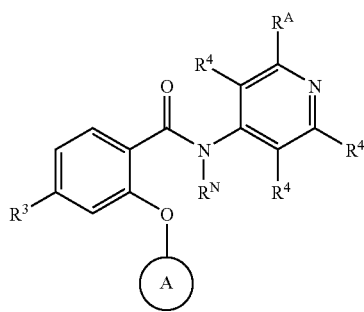

III-B

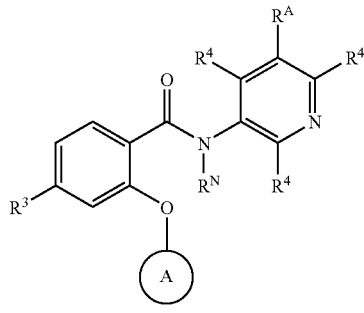

III-C or a pharmaceutically acceptable salt thereof, wherein Ring A, R$^3$, R$^5$, R$^N$, R$^A$ and R$^4$ are defined herein.

In some embodiments of compounds of formula III-A, III-B or III-C, R$^3$ is selected from hydrogen, halogen, CN, NO$_2$, or an optionally substituted group selected from C$_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In some embodiments of compounds of formula III-A, III-B or III-C, R$^3$ is selected from Cl, Br, F, CF$_3$, methyl, ethyl, isopropyl, t-butyl, isobutyl, CN, —COOH, —N(CH$_3$)$_2$, —N(Et)$_2$, —N(iPr)$_2$, —O(CH$_2$)$_2$OCH$_3$, —CONH$_2$, —COO(C$_{1-6}$ alkyl), —OH, —OCF$_3$, —SCF$_3$, —OCH$_3$, —CH$_2$OH, —NHCOCH$_3$, —SO$_2$NH$_2$, optionally substituted pyrrolyl, thiadiazolyl, pyridyl, imidazolyl, pyrazolyl, piperidinyl, piperazinyl, morpholinyl, or an optionally substituted group selected from C$_{1-4}$alkoxy, phenyl, phenyloxy, benzyl, or benzyloxy.

In some embodiments of compounds of formula III-A, III-B or III-C, R$^3$ is a C$_1$-C$_6$ alkyl group. In other embodiments, R$^3$ is selected from methyl, ethyl, isopropyl, t-butyl, or sec-butyl.

In some embodiments of compounds of formula III-A, III-B or III-C, R$^3$ is selected from an optionally substituted pyrrolyl, thiadiazolyl, pyridyl, imidazolyl, pyrazolyl, piperidinyl, piperazinyl, or morpholinyl.

In other embodiments of compounds of formula III-A, III-B or III-C, R$^3$ is selected from an optionally substituted phenyl, benzyl, phenyloxy, or benzyloxy.

In some embodiments of compounds of formula III-A, III-B or III-C, y is 0-4 and each R$^5$ group, when present, is independently selected from hydrogen, halogen, CN, NO$_2$, or an optionally substituted group selected from C$_{1-4}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —COOR', —C(O)R', —NRCOR', —CON(R')$_2$, or —S(O)$_2$N(R')$_2$.

In some embodiments of compounds of formula III-A, III-B or III-C, y is 1-3, and each R$^5$ is independently selected from CN, CF$_3$, —C(O)R', —COOR', —OR', —CON(R')$_2$, halogen, optionally substituted C$_{1-4}$ aliphatic, 5-6 membered heteroaryl, or 4-7 membered heterocyclyl.

In some embodiments of compounds of formula III-A, III-B or III-C, y is 1-3, and each R$^5$ is independently selected from CN, CF$_3$, —C(O)(C$_{1-4}$ alkyl), —COO(C$_{1-4}$ alkyl), —O(C$_{1-4}$ alkyl), —CON(R')$_2$, F, Cl, Br, ethyl, propyl, isopropyl, t-butyl, isobutyl, sec-butyl, optionally substituted pyridyl, pyrimidinyl, pyrazinyl, pyridazinyl, pyrazinyl, piperidinyl, morpholinyl, piperazinyl, pyrrolidinyl or azetidinyl.

In some embodiments of compounds of formula III-A, III-B or III-C, y is 1-3, and each R$^5$ is independently selected from CN, CF$_3$, —C(O)Me, —COOMe, —OMe, —CONH$_2$, F, Cl, Br, ethyl, propyl, isopropyl, t-butyl, isobutyl, sec-butyl, optionally substituted pyridyl, pyrimidinyl, pyrazinyl, pyridazinyl, pyrazinyl, piperidinyl, morpholinyl, piperazinyl, pyrrolidinyl, or azetidinyl.

In some embodiments of compounds of formula III-A, III-B or III-C, y is 1-3, and each R$^5$ is independently selected from CN, CF$_3$, —C(O)Me, —COOMe, —OMe, F, Cl, Br, isopropyl, t-butyl, isobutyl, sec-butyl, optionally substituted pyridyl, piperidinyl, or morpholinyl.

In some embodiments of compounds of formula III-A, III-B or III-C, each R$^4$, when present, is hydrogen.

In some other embodiments of compounds of formula III-A, III-B or III-C, each R$^4$, when present, is independently selected from hydrogen, halogen, CN, NO$_2$, or an optionally substituted group selected from C$_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In some embodiments of compounds of formula III-A, III-B or III-C, R$^A$ is selected from SO$_2$N(R$^2$)$_2$ or SO$_2$R$^1$. In other embodiments, R$^1$ is SO$_2$N(R$^2$)$_2$ and both R$^2$ are hydrogen. In yet other embodiments, R$^A$ is SO$_2$R$^1$ and R$^1$ is C$_{1-6}$ alkyl.

In some embodiments of compounds of formula III-A, III-B or III-C, ring A is optionally substituted phenyl. In other embodiments, ring A is an optionally substituted 5-7 membered heteroaryl ring.

In some embodiments of compounds of formula III-A, III-B or III-C, ring A is selected from:

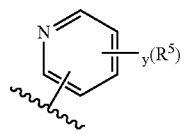
a

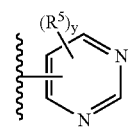
b

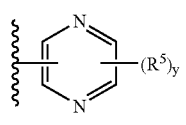
c

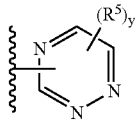
d

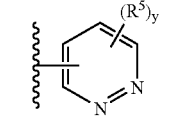
e

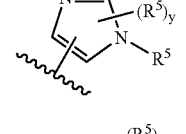
f

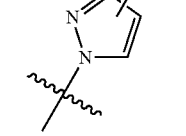
g

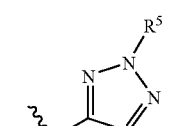
h

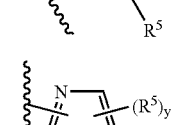
i

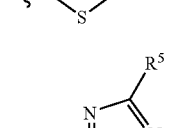
j

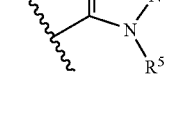

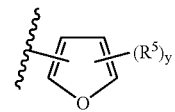
k

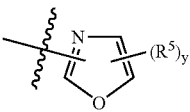
l

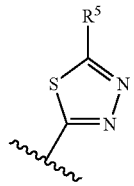
m

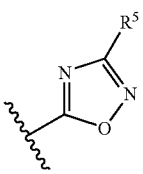
n

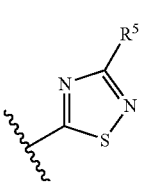
o

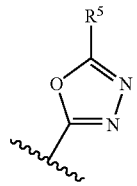
p

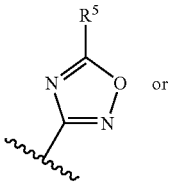 or
q

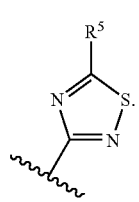
r

In other embodiments of compounds of formula III-A1, III-A2 or III-A3, ring A is either optionally substituted phenyl or

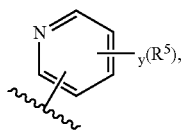

each $R^4$ is hydrogen, $R^A$ is $SO_2NH_2$ or $SO_2CH_3$, y is 1, $R^5$ is selected from methyl, $CF_3$, fluoro or chloro, $R^N$ is hydrogen and $R^3$ is $CF_3$ or t-butyl.

In some embodiments, the present invention provides a method of modulating a sodium channel comprising the step of contacting said channel with a compound of formula I:

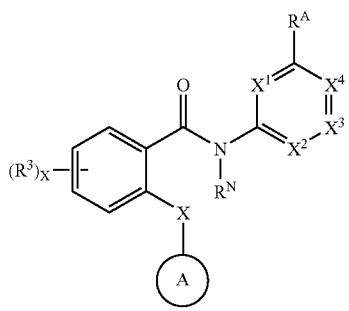

or a pharmaceutically acceptable salt thereof, wherein:
X is O, S, $NR^N$, C(O), or $C(R^N)_2$;
Ring A is phenyl or a 5-7 membered heteroaryl ring, wherein ring A is optionally substituted with up to y occurrences of $R^5$;
$X^1$, $X^2$, $X^3$ and $X^4$ are each independently nitrogen or C—$R^4$ provided that at least one of $X^1$, $X^2$, $X^3$ and $X^4$ is nitrogen and provided that $X^1$, $X^2$, $X^3$ and $X^4$ are not all simultaneously nitrogen;
$R^A$ is selected from $SO_2N(R^2)_2$, $SO_2R^1$, $NR^2SO_2R^1$;
$R^1$ is $C_{1-6}$ aliphatic, wherein up to two carbon atoms other than the atom attached to the nitrogen or oxygen atom is optionally replaced with O, S, $NR^N$, or C(O);
each $R^2$ is independently hydrogen, or $C_{1-6}$ aliphatic, wherein up to two carbon atoms other than the atom attached to the nitrogen or oxygen atom is optionally replaced with O, S, $NR^N$, or C(O); x is 0-4;
y is 0-4;
each occurrence of $R^N$ is independently selected from hydrogen or a $C_{1-6}$ aliphatic group optionally substituted with 1-3 independent occurrences of —$R^J$, oxo, thioxo, —$CO_2R^J$, —$OR^J$, —$N(R^J)_2$, —$SR^J$, —$NO_2$, halogen, —CN, —$C_{1-4}$haloalkyl, —$C_{1-4}$haloalkoxy, —C(O)N$(R^J)_2$, —$NR^JC(O)R^J$, —$SO_2R^J$, —$SO_2N(R^J)_2$, —$NR^JSO_2R^J$, —$NR^JCON(R^J)_2$, —$NR^JCO_2R^J$, —$COR^J$, —$OCOR^J$, —$OCON(R^J)_2$, —$SOR^J$, —$NR^JSO_2N(R^J)_2$, —$COCOR^J$, —$COCH_2COR^J$, —$OP(O)(OR^J)_2$, —$P(O)(OR^J)_2$, —$PO(OR^J)(R^J)$, —$P(O)(R^J)_2$, or —$OP(O)(R^J)_2$; wherein
$R^J$ is hydrogen or unsubstituted $C_{1-6}$ aliphatic;
each occurrence of $R^3$, $R^4$, and $R^5$ is independently Q-$R^X$;
Q is a bond or is a $C_{1-6}$ aliphatic chain wherein up to three methylene units of Q are optionally and independently replaced by —NH—, —NR—, —O—, —S—, —$CO_2$—, —OC(O)—, —C(O)CO—, —C(O)—, —C(S)—, —C(O)NH—, —C(O)NR—, —C(=N—CN)—, —NHCO—, —NRCO—, —NHC(O)O—, —NRC(O)O—, —$SO_2NH$—, —$SO_2NR$—, —$NHSO_2$—, —$NRSO_2$—, —NHC(O)NH—, —NRC(O)NH—, —NHC(O)NR—, —NRC(O)NR, —OC(O)NH—, —OC(O)NR—, —$NHSO_2NH$—, —$NRSO_2NH$—, —$NHSO_2NR$—, —$NRSO_2NR$—, —SO— or —$SO_2$—; wherein
Q is optionally substituted with 1-3 independent occurrences of $R^Q$;
each occurrence of $R^X$ is independently selected from —R', halogen, —$NO_2$, —CN, —OR', —SR', —N(R')$_2$, —NR'C(O)R', —NR'C(O)N(R')$_2$, —NR'$CO_2$R', —C(O)R', —$CO_2$R', —OC(O)R', —C(O)N(R')$_2$, —OC(O)N(R')$_2$, —SOR', —$SO_2$R', —$SO_2$N(R')$_2$, —NR'$SO_2$R', —NR'$SO_2$N(R')$_2$, —C(O)C(O)R', —C(O)CH$_2$C(O)R', —OP(O)(OR')$_2$, —P(O)(OR')$_2$, —PO(OR')(R'), —P(O)(R')$_2$, or —OP(O)(R')$_2$;
each occurrence of R is independently selected from hydrogen or a $C_{1-6}$ aliphatic group optionally substituted with 1-3 independent occurrences of —$R^T$, -T-$Ar^1$, halogen, oxo, thioxo, —$OR^T$, —$SR^T$, —$N(R^T)_2$, —$NO_2$, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$; wherein
each $R^T$ is independently hydrogen or unsubstituted $C_{1-6}$ aliphatic; or
any two $R^T$ groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of —$R^R$, -T-$Ar^1$, halogen, oxo, thioxo, —$OR^R$, —$SR^R$, —$N(R^R)_2$, —$NO_2$, —$C_{1-4}$haloalkyl, —$C_{1-4}$haloalkoxy, —CN, —$CO_2R^R$, —$COR^R$, —$CON(R^R)_2$, —$OCOR^R$, —$NR^RCOR^R$, —$SO_2R^R$, —$SO_2N(R^R)_2$, or —$NR^RSO_2R^R$; wherein
each $R^R$ is independently hydrogen or unsubstituted $C_{1-6}$ aliphatic;
T is $(CH_2)_w$;
w is 0-2;
$Ar^1$ is selected from a 3-8 membered saturated or partially unsaturated ring, a 5-6 membered aryl ring, a 3-7 membered heterocyclic ring having 1-3 heteroatoms independently selected from nitrogen, oxygen, or sulfur, a 5-6 membered heteroaryl ring having 1-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein
$Ar^1$ is optionally substituted with 1-3 independent occurrences of —$R^W$, oxo, thioxo, —$CO_2R^W$, —$OR^W$, —$N(R^W)_2$, —$SR^W$, —$NO_2$, halogen, —CN, —$C_{1-4}$haloalkyl, —$C_{1-4}$haloalkoxy, —C(O)N$(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$PO(OR^W)(R^W)$, —$P(O)(R^W)_2$, or —$OP(O)(R^W)_2$; wherein
$R^W$ is hydrogen or unsubstituted $C_{1-6}$ aliphatic;
$R^Q$ is selected from halogen, —$R^S$, —$N(R^S)_2$, —SRS, —ORS, $C_{3-10}$ cycloaliphatic, $C_{6-10}$ aryl, 5-10 membered heteroaryl, 5-10 membered heterocyclyl, oxo, thioxo, —$C_{1-4}$haloalkoxy, —$C_{1-4}$haloalkyl, —$NO_2$, —CN, —CF₃, —OCF₃, —CO₂Rˢ, —CORˢ, —OC(O)Rˢ or —NRˢC(O)Rˢ; wherein R^S is hydrogen or unsubstituted $C_{1-6}$ aliphatic; or any two $R^Q$ or two $R^S$ groups, or any combination of an $R^Q$ group with an $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, halogen, oxo, thioxo, —OR^O, —SRO, —N(R^O)₂, —NO₂, —$C_{1-4}$haloalkyl, —$C_{1-4}$haloalkoxy, —CN, —CO₂R^O, —COR^O, —CON(R^O)₂, —OCOR^O, —NR^OCOR^O, —SO₂R^O, —SO₂N(R^O)₂, or —NR^OSO₂R^O; wherein $R^O$ is hydrogen or unsubstituted $C_{1-6}$ aliphatic; and each occurrence of R' is independently selected from hydrogen or a $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; wherein said $C_{1-8}$ aliphatic, $C_{6-10}$ aryl, heteroaryl ring or heterocyclyl ring is optionally substituted with 1-3 independent occurrences of $R^I$, halogen, oxo, thioxo, —OR^I, —SR^I —N(R^I)₂, —NO₂, —$C_{1-4}$haloalkyl, —$C_{1-4}$haloalkoxy, —CN, —CO₂R^I, —COR^I, —CONHR^I, —OCOR^I, —NR^ICOR^I, —SO₂R^I, —SO₂N(R^I)₂, or —NR^ISO₂R^I; wherein $R^I$ is hydrogen or unsubstituted $C_{1-6}$ aliphatic.

In some embodiments of formula I of the method, x is 0-2. In other embodiments, x is 2. In yet other embodiments, x is 1.

In some embodiments of formula I of the method, x is 1-3, and each $R^3$ is independently selected from hydrogen, halogen, CN, CF₃, NO₂, or an optionally substituted group selected from $C_{1-6}$ aliphatic, $C_{1-6}$ cycloaliphatic, $C_{6-10}$ aryl, 5-6 membered heteroaryl, 4-7 membered heterocyclyl, aralkyl, —N(R')₂, —CH₂N(R')₂, —OR', —CH₂OR', —SR', —CH₂SR', —C(O)R', —COOR', —NRCOR', —CON(R')₂, —S(O)₂R', or —S(O)₂N(R')₂.

In some embodiments of formula I of the method, x is 1-3, and each $R^3$ is independently selected from Cl, Br, F, CF₃, methyl, ethyl, propyl, isopropyl, t-butyl, isobutyl, sec-butyl, cyclopropyl, cyclobutyl, cyclopentyl, cyclohexyl, CN, NO₂, —COOH, —N(CH₃)₂, —N(Et)₂, —N(iPr)₂, —O(CH₂)₂OCH₃, —CONH₂, —COO($C_{1-6}$ alkyl), —OH, —OCF₃, —SCF₃, —OCH₃, —CH₂OH, —NHCOCH₃, —SO₂NH₂, —SO₂CH₃, methylenedioxy, ethylenedioxy, or an optionally substituted group selected from pyrrolyl, thiadiazolyl, pyridyl, imidazolyl, pyrazolyl, piperidinyl, piperazinyl, morpholinyl, 2-oxo-imidazolidyl, $C_{1-4}$ alkoxy, phenyl, phenylethyl, phenyloxy, phenyloxymethyl, phenylformyl, benzyl, benzylamino, or benzyloxy.

In some embodiments of formula I of the method, y is 1-3, and each $R^5$ is independently selected from halogen, CN, NO₂, or an optionally substituted group selected from $C_{1-4}$ aliphatic, aryl, 5-6 membered heteroaryl, 4-7 membered heterocyclyl, aralkyl, —N(R')₂, —CH₂N(R')₂, —OR', —CH₂OR', —SR', —CH₂SR', —COOR', —NRCOR', —CON(R')₂, or —S(O)₂N(R')₂.

In some embodiments of formula I of the method, y is 1-3, and each $R^5$ is independently selected from Cl, Br, F, CF₃, methyl, ethyl, CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, methylenedioxy, ethylenedioxy, piperidinyl, piperazinyl, morpholino, or an optionally substituted group selected from $C_{1-4}$alkoxy, phenyl, phenyloxy, benzyl, or benzyloxy.

In some embodiments of formula I of the method, radical:

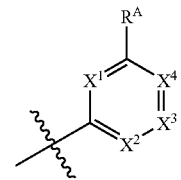

is selected from:

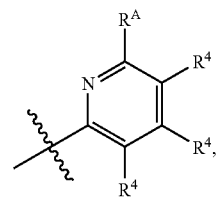

a-1

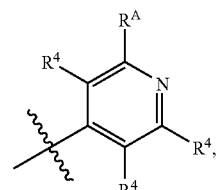

a-2

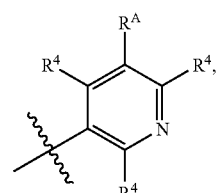

a-3

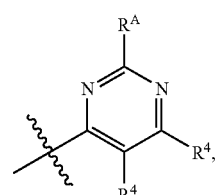

b-1

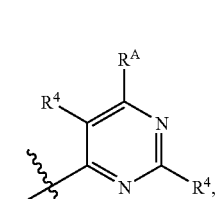

b-2

-continued

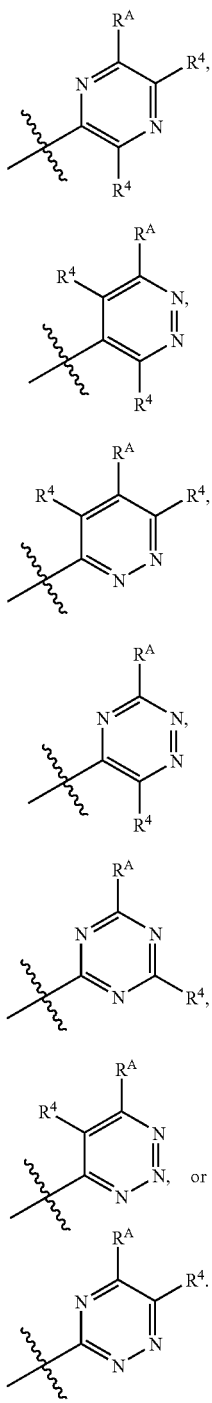

c-1 e-1 e-2 d-1 d-2 d-3 d-4

In some other embodiments of formula I of the method, radical:

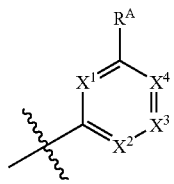

is selected from ring a-1, a-2 or a-3.

In some embodiments of formula I of the method, each $R^4$ is hydrogen.

In some other embodiments of formula I of the method, each $R^4$, when present, is independently selected from hydrogen, halogen, CN, $NO_2$, or an optionally substituted group selected from $C_{1-6}$ aliphatic, aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NR'COR', —CON(R')$_2$, or —S(O)$_2$N(R')$_2$.

In some embodiments of formula I of the method, $R^A$ is selected from $SO_2N(R^2)_2$ or $SO_2R^1$. In other embodiments, $R^1$ is $SO_2N(R^2)_2$ and both $R^2$ are hydrogen. In yet other embodiments, $R^1$ is $SO_2R^1$ and $R^1$ is $C_{1-6}$ alkyl.

In some embodiments of formula I of the method, ring A is optionally substituted phenyl. In other embodiments, ring A is an optionally substituted 5-7 membered heteroaryl ring.

In other embodiments of formula I of the method, ring A is selected from:

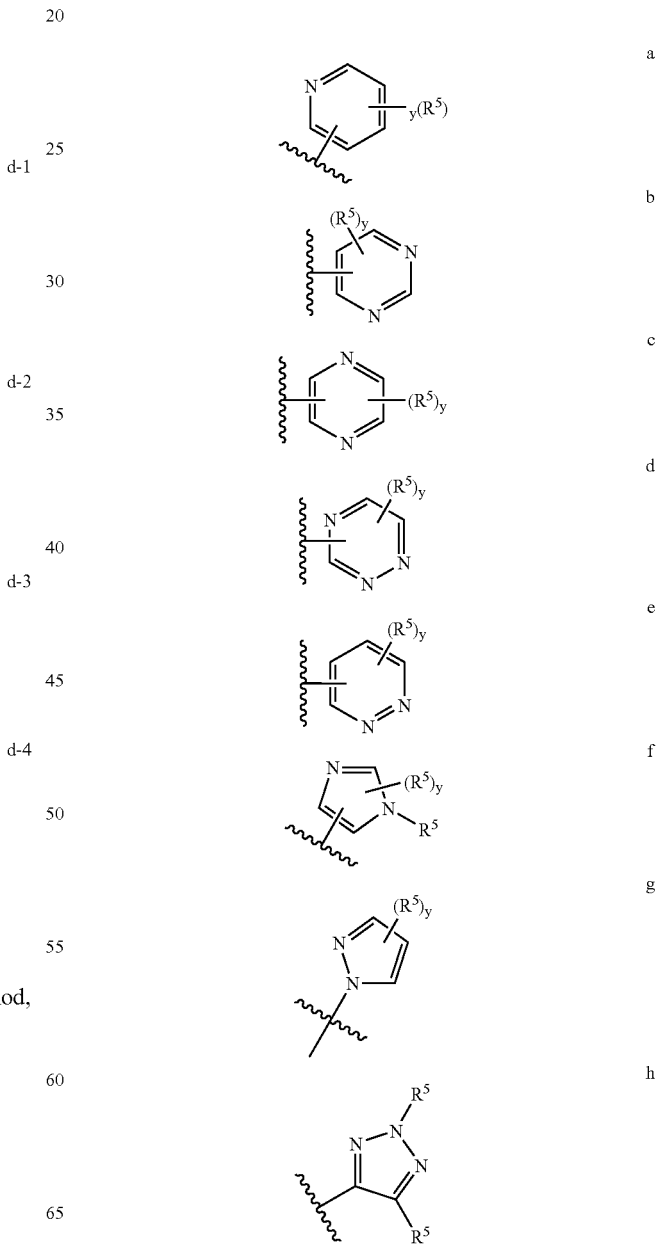

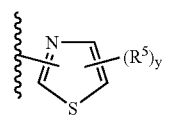 i
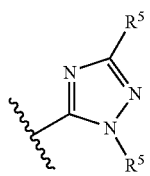 j
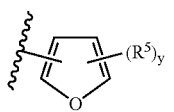 k
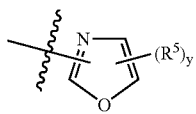 l
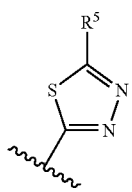 m
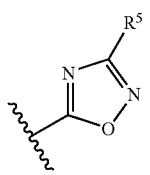 n
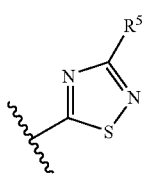 o
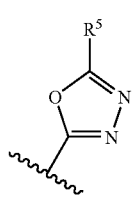 p
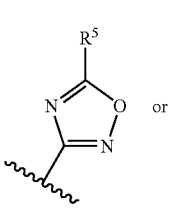 or
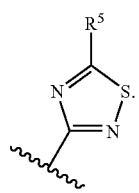 r
In another embodiment, any of the embodiments described herein for compounds of formula I, I-A, II-A1, II-A2, II-A3, III-A, III-B or III-C are applicable to the compounds described in the methods of the present invention.
In other embodiments of the present invention, a compound has the structure of a compound in Table 1 below.
TABLE 1
Compounds of formula I:
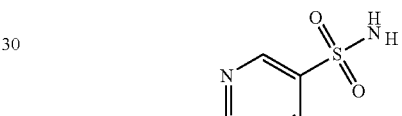
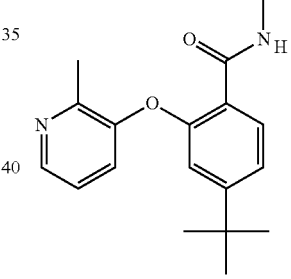
1
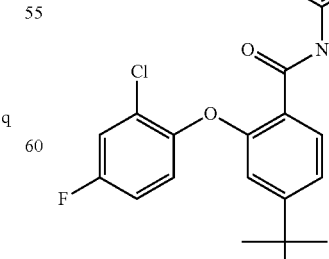
2

TABLE 1-continued
Compounds of formula I:
3
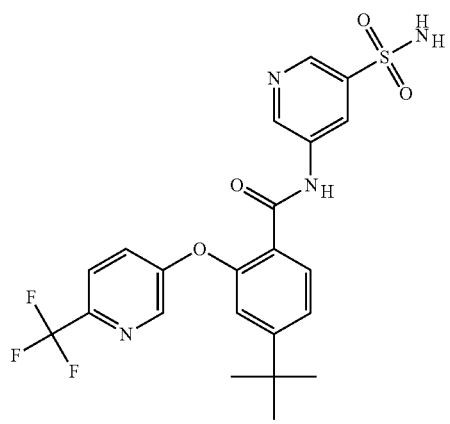
4
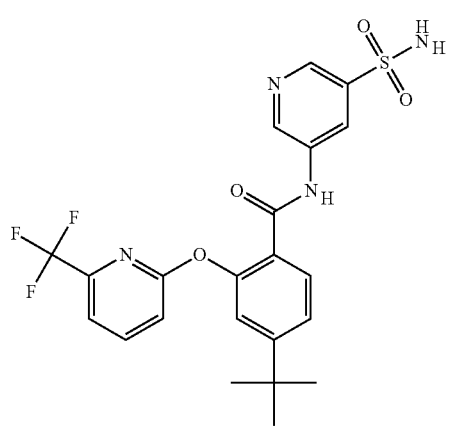
5
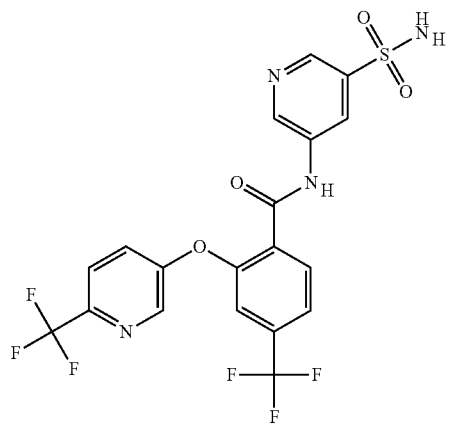
TABLE 1-continued
Compounds of formula I:
6
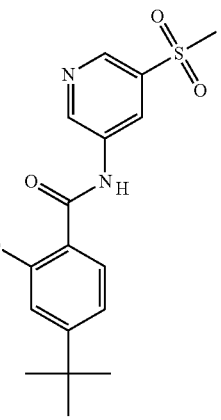
7
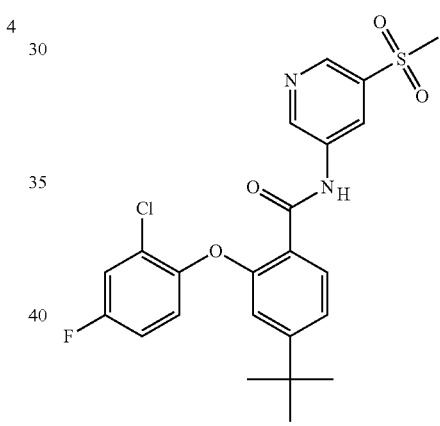
8
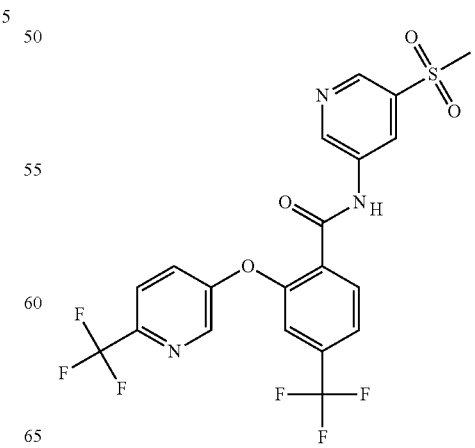

TABLE 1-continued

Compounds of formula I:

9

[Chemical structure of compound 9]

Compositions, Formulations, and Administration of Compounds of the Invention

In another embodiment, the invention provides a pharmaceutical composition comprising a compound of any of the formulae or classes described herein. In a further embodiment, the invention provides a pharmaceutical composition comprising a compound of Table 1.

In another embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit voltage-gated sodium ion channels. Thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence, in a biological sample or in a patient. Preferably the composition of this invention is formulated for administration to a patient in need of such composition. Most preferably, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In some embodiments, the invention relates to a method of inhibiting sodium channel activity in a biological sample comprising the step of contacting said biological sample with a compound of this invention, or a composition comprising said compound. The term "biological sample," as used herein, means a sample outside a living organism and includes, without limitation, cell cultures or extracts thereof, biopsied material obtained from a mammal or extracts thereof, and blood, saliva, urine, feces, semen, tears, or other body fluids or extracts thereof. Inhibition of sodium channel activity in a biological sample is useful for a variety of purposes known to one of skill in the art. Examples of such purposes include, but are not limited to, biological specimen storage and biological assays. In one embodiment, the method of inhibiting sodium channel activity in a biological sample is limited to non-therapeutic methods.

In some embodiments, the invention relates to a method for treating or lessening the severity in a subject of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abnormal gastro-intestinal motility, comprising administering an effective amount of a compound of the present invention, or a pharmaceutically acceptable composition comprising a compound to a subject in need thereof.

The term "subject", as used herein, means an animal, preferably a mammal, and most preferably a human.

In some embodiments, the invention relates to a method for treating or lessening the severity of acute, chronic, neuropathic, or inflammatory pain.

In another embodiment, the invention relates to a method for treating or lessening the severity of radicular pain, sciatica, back pain, head pain, neck pain, intractable pain, acute pain, postsurgical pain, back pain, tinnitus or cancer pain.

In another embodiment, the invention relates to a method for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; or angina-induced pain.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8 or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8 or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8 or NaV1.9, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8 or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8 or NaV1.9, may be assayed according to methods described generally in the Examples herein, or according to methods available to one of ordinary skill in the art.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999; The Merck Manual, Eighteenth Edition, Ed. Mark H. Beers and Robert S. Porter, Merck Research Laboratories, 2006 and the Food and Drug Administration website, www.fda.gov, the entire contents of which are hereby incorporated by reference.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

Another aspect of the invention relates to inhibiting NaV1.1, NaV1.2, NaV1.3, NaV1.4, NaV1.5, NaV1.6, NaV1.7, NaV1.8 or NaV1.9 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of NaV1.1, NaV1.2, NaV1.3, NaV1.4, NaV1.5, NaV1.6, NaV1.7, NaV1.8 or NaV1.9 activity in a biological sample is useful for a variety of purposes that are known to one of skill in the art. Examples of such purposes include, but are not limited to, biological specimen storage, biological assays, the study of sodium ion channels in biological and pathological phenomena; and the comparative evaluation of new sodium ion channel inhibitors. In one embodiment, the method of inhibiting sodium channel activity in a biological sample is limited to non-therapeutic methods.

In order that the invention described herein may be more fully understood, the following examples are set forth. It should be understood that these examples are for illustrative purposes only and are not to be construed as limiting this invention in any manner.

Preparation of Compounds of the Invention

The following definitions describe terms and abbreviations used herein:

| | |
|---|---|
| Ac | acetyl |
| Bu | butyl |
| Et | ethyl |
| Ph | phenyl |
| Me | methyl |
| Boc | t-butyloxycarbonyl |
| THF | tetrahydrofuran |
| DCM | dichloromethane |
| $CH_2Cl_2$ | dicloromethane |
| EtOAc | ethyl acetate |
| $CH_3CN$ | acetonitrile |
| EtOH | ethanol |
| MeOH | methanol |
| DMF | N,N-dimethylformamide |
| DMSO | dimethyl sulfoxide |
| HOAc | acetic acid |
| TFA | trifluoroacetic acid |
| BOP | (benzotriazol-1-yloxytris(dimethylamino)phosphonium hexafluorophosphate) |
| EDC | 1-(3-dimethylaminopropyl)-3-ethylcarbodiimide hydrochloride |
| 4-DMAP | 4-dimethylaminopyridine |
| HATU | (N-[(dimethylamino)-1-H-1,2,3-triazolo[4,5,6]-pyridin-1-ylmethylene]-N-methylmethanaminium hexafluorophosphate N-oxide) |
| $SOCl_2$ | thionyl chloride |
| $Et_3N$ | triethylamine |
| DIPEA | diisopropylethylamine |
| DIEA | diisopropylethylamine |
| $K_2CO_3$ | potassium carbonate |
| $Na_2CO_3$ | sodium carbonate |
| $Cs_2CO_3$ | cesium carbonate |
| $Na_2SO_4$ | sodium sulfate |
| $CuSO_4$ | copper sulfate |
| $(CuOTf)_2 \cdot PhH$ | copper (I) triflate benzene complex |
| $NaHCO_3$ | sodium bicarbonate |
| NaOH | sodium hydroxide |
| KOH | potassium hydroxide |
| LiOH | lithium hydroxide |
| 4Å MS | 4 angstom molecular sieves |
| LC/MS | liquid chromatography/mass spectra |
| HPLC | high performance liquid chromtagraphy |
| hr | hours |
| atm | atmospheres |
| rt or RT | room temperature |

As used herein, other abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

General Synthetic Procedures

In general, the compounds of this invention may be prepared by methods described herein or known to those skilled in the art for the preparation of analogous compounds. The following non-limiting schemes and examples are presented to further exemplify the invention. It should be understood that these examples are for illustrative purposes only and are not to be construed as limiting this invention in any manner.

Schemes A and B below illustrate exemplary processes for preparing compounds of formula I. Scheme A was used to prepare compounds I-5 in Table 1 of the present invention. Scheme B was used to prepare compounds 6-9 in Table 1 of the present invention. However, the acid intermediates used in Scheme B were prepared according to the procedure in Scheme A.

Scheme A:

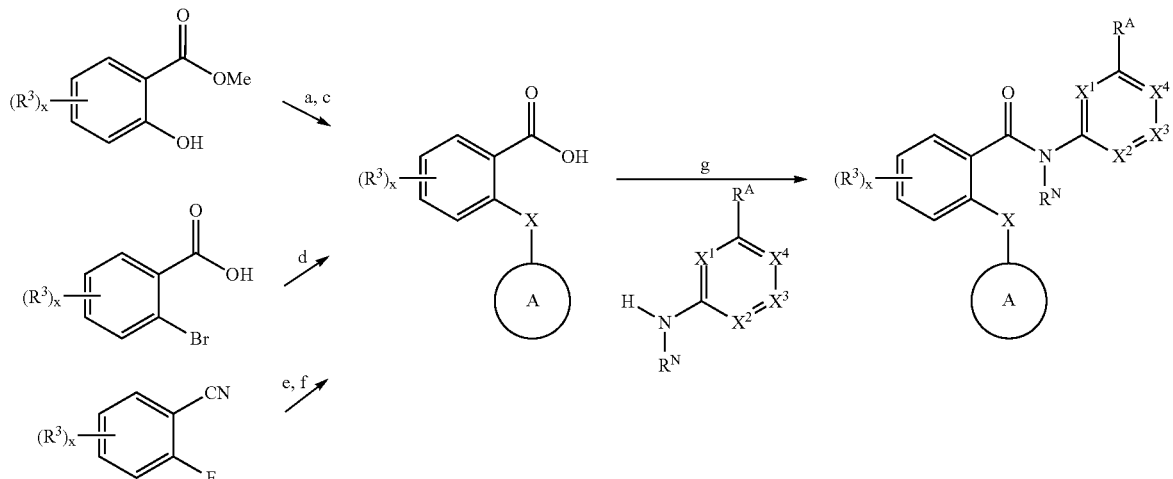

Conditions: (a) Ring-A—F, Cs$_2$CO$_3$, DMF; (c) LiOH, THF, H$_2$O; (d) Ring-A—XH, (CuOTf)$_2$•PhH, Cs$_2$CO$_3$, 1-naphthoic acid, 4 Å MS, toluene, EtOAc; (e) Ring-A—XH, Cs$_2$CO$_3$, DMF; (f) HCl, dioxane, H$_2$O or NaOH, EtOH, H$_2$O; (g) HATU, Et$_3$N, DMF or BOP, Et$_3$N, CH$_2$Cl$_2$ or SOCl$_2$, CH$_2$Cl$_2$, pyridine Scheme B:

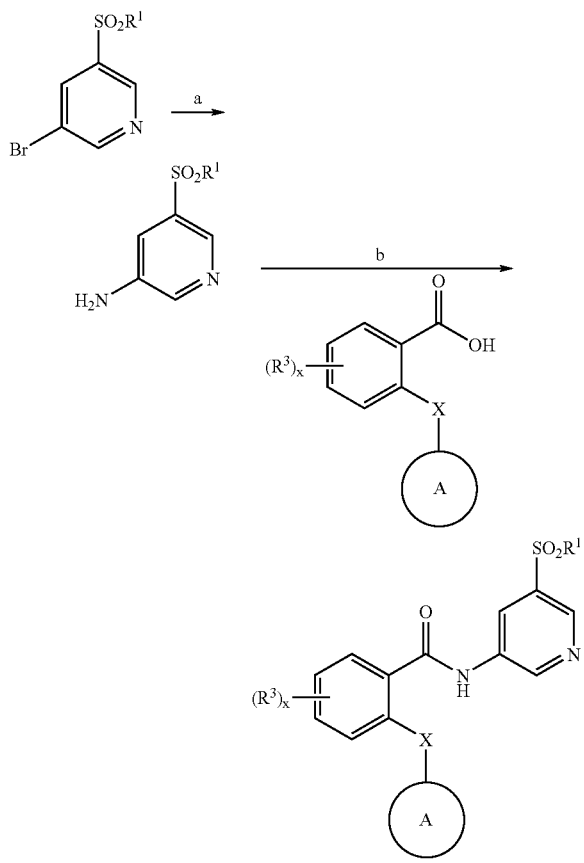

Conditions: (a) CuSO4•(H2O)5, NH4OH; (b) HATU, Et$_3$N, DMF or BOP, Et$_3$N, CH$_2$Cl$_2$ or SOCl$_2$, toluene, pyridine Examples of suitable peptide coupling reagents include DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl)-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-CL (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one), or PyBrOP (bromotris(pyrrolidino)phosphonium hexafluorophosphate). Optional reagents that may be used in the amide bond-forming reaction include 4-DMAP (4-dimethylaminopyridine) or active ester reagents, such as HOBT (1-hydroxybenzotriazole), HOAT (hydroxyazabenzotriazole), HOSu (hydroxysuccinimide) and HONB (endo-N-hydroxy-5-norbornene-2,3-dicarboxamide).

SYNTHETIC EXAMPLES

General Methods $^1$H NMR (400 MHz) and $^{13}$C NMR (100 MHz) spectra were obtained as solutions in deuteriochloroform (CDCl$_3$) or dimethyl sulfoxide-D$_6$ (DMSO). LC/MS data were acquired using a PESciex API-150-EX LC/MS, Shimadzu LC-8A pumps, Gilson 215 autosampler, Gilson 819 injection module, 3.0 mL/min flow rate, 10-99% CH$_3$CN (0.035% TFA)/ H$_2$O (0.05% TFA) gradient, Phenomenex Luna 5 μm C18 column (50×4.60 mm), Shimadzu SPD-10A UV/Vis detector, Cedex 75 ELSD detector. Silica gel chromatography was performed using silica gel-60 with a particle size of 230-400 mesh. Pyridine, dichloromethane, and tetrahydrofuran were from Aldrich Sure-Seal bottles kept under dry nitrogen. All reactions were stirred magnetically unless otherwise noted. Unless specified otherwise, all temperatures refer to internal reaction temperatures.

The following preparative examples are set forth in order that this invention be more fully understood. These examples are for the purpose of illustration only and are not to be construed as limiting the scope of the invention in any way.

Methyl 4-tert-butyl-2-(6-(trifluoromethyl)pyridin-2-yloxy)benzoate

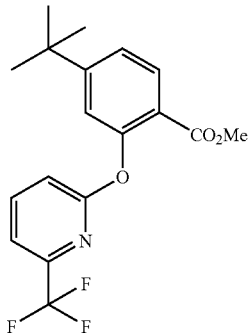 [SMILES: COC(=O)c1ccc(C(C)(C)C)cc1Oc1cccc(C(F)(F)F)n1]

A mixture of methyl 4-tert-butyl-2-hydroxybenzoate (0.70 g, 3.4 mmol), 2-fluoro-6-(trifluoromethyl)pyridine (0.55 g, 3.4 mmol), and $Cs_2CO_3$ (1.1 g, 3.4 mmol) in DMF (15 mL) was heated at 70° C. for 19 hours. The reaction was diluted with water and extracted with ethyl acetate. The combined extracts were washed with brine and water, dried over sodium sulfate, and evaporated. The residue was purified by column chromatography on silica gel with 0-15% ethyl acetate in hexanes to give methyl 4-tert-butyl-2-(6-(trifluoromethyl)pyridin-2-yloxy)benzoate (0.49 g, 41% yield). LC/MS: m/z 354.3 (M+H)$^+$ at 2.13 min (10%-99% $CH_3CN$ (0.035% TFA)/$H_2O$ (0.05% TFA)).

4-tert-Butyl-2-(6-(trifluoromethyl)pyridin-2-yloxy)benzoic acid

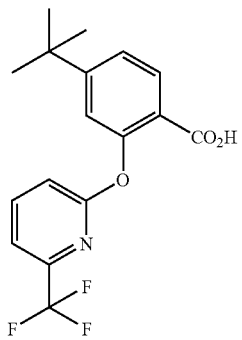 [SMILES: CC(C)(C)c1ccc(C(=O)O)c(Oc2cccc(C(F)(F)F)n2)c1]

A mixture of methyl 4-tert-butyl-2-(6-(trifluoromethyl)pyridin-2-yloxy)benzoate (0.49 g, 1.4 mmol) and lithium hydroxide hydrate (0.12 g, 2.8 mmol) in THF (5 mL) and water (5 mL) was stirred at room temperature for two days. The reaction was made acidic with 1 M HCl(aq) and extracted with ethyl acetate. The combined extracts were washed with water, dried over sodium sulfate, and evaporated to give 4-tert-butyl-2-(6-(trifluoromethyl)pyridin-2-yloxy)benzoic acid (0.45 g, 95% yield). LC/MS: m/z 340.5 (M+H)$^+$ at 1.89 min (10%-99% $CH_3CN$ (0.035% TFA)/$H_2O$ (0.05% TFA)). $^1$H NMR (400 MHz, $CDCl_3$) δ 8.00 (d, J=8.3 Hz, 1H), 7.85-7.81 (m, 1H), 7.36-7.33 (m, 2H), 7.26-7.24 (m, 1H), 7.09 (d, J=8.4 Hz, 1H) and 1.34 (s, 9H) ppm.

4-tert-Butyl-2-(2-chloro-4-fluorophenoxy)benzoic acid

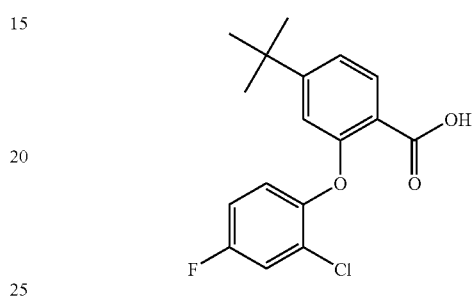

In a pressure-vessel, a stirring mixture of 2-bromo-4-tert-butylbenzoic acid (1.00 g, 3.89 mmol) and 2-chloro-4-fluorophenol (860 mg, 620 µL, 5.87 mmol) in toluene (20 mL) was added $Cs_2CO_3$ (2.53 g, 7.78 mmol) followed by copper(I) triflate benzene complex (98 mg, 0.19 mmol). The sealed vessel was heated to 120° C. for 16 h. After cooling to room temperature, the reaction mixture was partitioned between 50 mL EtOAc and 50 mL $H_2O$. The aqueous layer was acidified using 2.0 N $HCl_{(aq)}$ and re-extracted with EtOAc. The combined organic solution was dried over $Na_2SO_4$, filtered, and concentrated. The residue was purified via silica gel chromatography using 0-3% MeOH/$CH_2Cl_2$ to give the product, 4-tert-butyl-2-(2-chloro-4-fluorophenoxy)benzoic acid as a white solid (907 mg, 2.81 mmol) in 72% yield. LC/MS: m/z 323.2 (M+H)$^+$ at 1.99 min (10%-99% $CH_3CN$ (0.035% TFA)/$H_2O$ (0.05% TFA)).

4-(Trifluoromethyl)-2-(6-(trifluoromethyl)pyridin-3-yloxy)benzonitrile

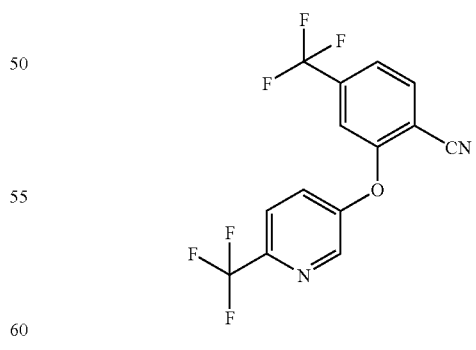

A mixture of 2-fluoro-4-(trifluoromethyl)benzonitrile (0.19 g, 1.0 mmol), 6-(trifluoromethyl)pyridin-3-ol (0.16 g, 1.0 mmol), and $Cs_2CO_3$ (0.33 g, 1 mmol) in DMF (10 mL) was stirred at 60° C. for 18 hours. The reaction was diluted with water and extracted with ethyl acetate. The combined extracts were washed with brine and water, dried over sodium sulfate, and evaporated. The residue was purified by column chromatography on silica gel with 0-15% ethyl acetate in hexanes to give 4-(trifluoromethyl)-2-(6-(trifluoromethyl)pyridin-3-yloxy)benzonitrile (0.29 g, 87% yield). LC/MS: m/z 333.5 (M+H)$^+$ at 1.83 min (10%-99% CH$_3$CN (0.035% TFA)/H$_2$O (0.05% TFA)).

4-(Trifluoromethyl)-2-(6-(trifluoromethyl)pyridin-3-yloxy)benzoic acid

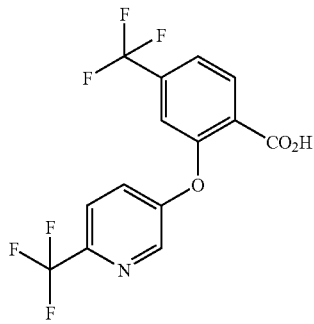 [SMILES: O=C(O)c1ccc(C(F)(F)F)cc1Oc1ccc(C(F)(F)F)nc1]

A solution of 4-(trifluoromethyl)-2-(6-(trifluoromethyl)pyridin-3-yloxy)benzonitrile in 4 M HCl in dioxane was stirred at 70° C. overnight and then at 90° C. for a day. The solvent was evaporated, and the residue was purified by preparative reverse phase HPLC using 10%-99% CH$_3$CN (0.035% TFA)/H$_2$O (0.05% TFA) to give 4-(trifluoromethyl)-2-(6-(trifluoromethyl)pyridin-3-yloxy)benzoic acid (28 mg, 47% yield). LC/MS: m/z 352.3 (M+H)$^+$ at 1.70 min (10%-99% CH$_3$CN (0.035% TFA)/H$_2$O (0.05% TFA)).

N-(5-Sulfamoylpyridin-3-yl)-4-(trifluoromethyl)-2-(6-(trifluoromethyl)pyridin-3-yloxy)benzamide
(Compound 5)

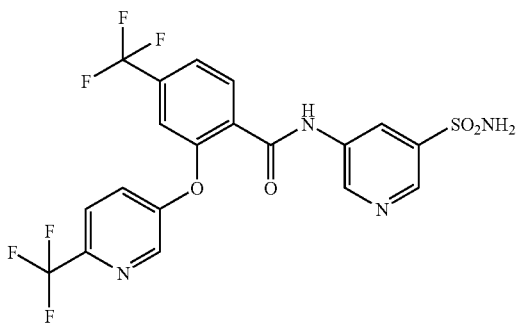 [SMILES: NS(=O)(=O)c1cncc(NC(=O)c2ccc(C(F)(F)F)cc2Oc2ccc(C(F)(F)F)nc2)c1]

A solution of 4-(trifluoromethyl)-2-(6-(trifluoromethyl)pyridin-3-yloxy)benzoic acid (28 mg, 81 μmol), HATU (31 mg, 81 μmol), and Et$_3$N (11 μL, 81 μmol) in DMF (1.0 mL) was stirred at room temperature for 5 min, then 5-aminopyridine-3-sulfonamide (14 mg, 81 μmol) was added. The reaction was stirred at room temperature then overnight at 70° C. The reaction was purified by reverse phase HPLC (10%-99% CH$_3$CN (0.035% TFA)/H$_2$O (0.05% TFA)) to give N-(5-sulfamoylpyridin-3-yl)-4-(trifluoromethyl)-2-(6-(trifluoromethyl)pyridin-3-yloxy)benzamide. LC/MS: m/z 507.3 (M+H)$^+$ at 1.61 min (10%-99% CH$_3$CN (0.035% TFA)/H$_2$O (0.05% TFA)).

5-(Methylsulfonyl)pyridin-3-amine

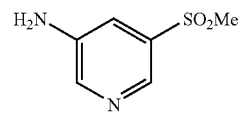

A mixture of 3-bromo-5-(methylsulfonyl)pyridine (0.50 g, 2.1 mmol) and CuSO$_4$ (H$_2$O)$_5$ (53 mg, 0.21 mmol) in concentrated ammonium hydroxide (3 mL) was heated in a sealed tube at 170° C. for 16 hours. The reaction was cooled to room temperature and extracted with ethyl acetate. The combined extracts were dried over sodium sulfate and evaporated to give a brown solid. The solid was purified by column chromatography on silica gel using 0-5% MeOH in dichloromethane to give 5-(methylsulfonyl)pyridin-3-amine (0.11 g, 31% yield) as a tan solid. LC/MS: m/z 173.3 (M+H) at 0.21 min (10%-99% CH$_3$CN (0.035% TFA)/H$_2$O (0.05% TFA)).

4-tert-Butyl-N-(5-(methylsulfonyl)pyridin-3-yl)-2-(6-(trifluoromethyl)pyridin-3-yloxy)benzamide
(Compound 6)

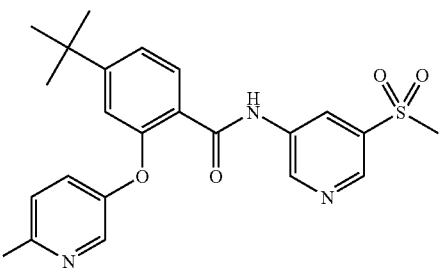

A stirring solution of 4-tert-butyl-2-(6-(trifluoromethyl)pyridin-3-yloxy)benzoic acid (21 mg, 61 μmol) in CH$_2$Cl$_2$ (0.50 mL) was treated with thionyl chloride (0.50 mL, 6.9 mmol) for 2 h. The mixture was concentrated on rotary evaporator. To the resulting residue was immediately added a solution of 5-(methylsulfonyl)pyridin-3-amine (12 mg, 67 μmol) in pyridine (0.50 mL). The reaction was allowed to stir at room temperature for 2 h, and then the pyridine was removed in vacuo. The mixture was redistributed between H$_2$O and CH$_2$Cl$_2$. The organic layer was dried over Na$_2$SO$_4$, filtered and concentrated. Purification using reverse phase HPLC reverse phase HPLC (10%-99% CH$_3$CN (0.035% TFA)/H$_2$O (0.05% TFA)) gave 4-tert-butyl-N-(5-(methylsulfonyl)pyridin-3-yl)-2-(6-(trifluoromethyl)pyridin-3-yloxy)benzamide as the TFA salt. LC/MS: m/z 494.2 (M+H) at 1.92 min (10%-99% CH$_3$CN (0.035% TFA)/H$_2$O (0.05% TFA)).

Analytical Characterization Data for compounds of Table 1 are show below in Table 2. The term "RT" stands for retention time in minutes.

TABLE 2

| Cmpd No. | LC-MS M + 1 | LC-RT min |
|---|---|---|
| 1 | 441.2 | 1.15 |
| 2 | 478 | 1.97 |
| 3 | 495.4 | 1.82 |
| 4 | 495.5 | 1.80 |
| 5 | 507.3 | 1.61 |
| 6 | 494.2 | 1.92 |
| 7 | 477.2 | 2.07 |
| 8 | 506.3 | 1.69 |
| 9 | 494.5 | 1.88 |

Biological Assays of Compounds of the Invention

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading
1) 24 hours before the assay on VIPR, CHO cells endogenously expressing a NaV1.2 type voltage-gated NaV are seeded in 96-well poly-lysine coated plates at 60,000 cells per well.
2) On the day of the assay, medium is aspirated and cells are washed twice with 225 µL of Bath Solution #2 (BS#2).
3) A 15 uM CC2-DMPE solution is prepared by mixing 5 mM coumarin stock solution with 10% Pluronic 127 1:1 and then dissolving the mix in the appropriate volume of BS#2.
4) After bath solution is removed from the 96-well plates, the cells are loaded with 80 µL of the CC2-DMPE solution. Plates are incubated in the dark for 30 minutes at room temperature.
5) While the cells are being stained with coumarin, a 15 µL oxonol solution in BS#2 is prepared. In addition to DiSBAC$_2$(3), this solution should contain 0.75 mM ABSC1 and 30 µL veratridine (prepared from 10 mM EtOH stock, Sigma #V-5754).
6) After 30 minutes, CC2-DMPE is removed and the cells are washed twice with 225 µL of BS#2. As before, the residual volume should be 40 µL.
7) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.
8) Once the incubation is complete, the cells are ready to be assayed on VIPR® with a sodium addback protocol. 120 µL of Bath solution #1 is added to stimulate the NaV dependent depolarization. 200 µL tetracaine was used as a positive control for complete block of the NaV channel.

Analysis of VIPR® Data:

Na$^+$ addback analysis windows: baseline 2-7 sec, final 15-24 sec.

$$\% \ Activity_{Na^+} = \frac{Signal_{Na^+}(Assay) - Signal_{Na^+}(Tetracaine)}{Signal_{Na^+}(DMSO) - Signal_{Na^+}(Tetracaine)} * 100\%$$

Solutions [mM]
Bath Solution #1: NaCl 160, KCl 4.5, CaCl$_2$ 2, MgCl$_2$ 1, HEPES 10, pH 7.4 with NaOH
Bath Solution #2 TMA-Cl 160, CaCl$_2$ 0.1, MgCl$_2$ 1, HEPES 10, pH 7.4 with KOH (final K concentration ~5 mM)
CC2-DMPE: prepared as a 5 mM stock solution in DMSO and stored at −20° C.
DiSBAC$_2$(3): prepared as a 12 mM stock in DMSO and stored at −20° C.
ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:
100 mg/mL Pluronic F-127 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSC1 in H$_2$O
Hank's Balanced Salt Solution (Hyclone #SH30268.02) supplemented with 10 mM HEPES (Gibco #15630-080)
Loading Protocol:
2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 L of 2×CC2-DMPE is to wells containing washed cells, resulting in a 10 μM final staining concentration. The cells are stained for 30 minutes in the dark at RT.

2×DISBAC$_2$(3) with ABSC1=6 μM DISBAC$_2$(3) and 1 mM ABSC1: The required amount of 10 mM DISBAC$_2$(3) is added to a 50 ml conical tube and mixed with 1 μL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 μL. Add 50 uL/well of the 2×DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay Buffer #1

140 mM NaCl, 4.5 mM KCl, 2 mM CaCl$_2$, 1 mM MgCl$_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water Assay Protocol 1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460nm} - background_{46nm})}{(intensity_{580nm} - background_{580nm})}$$

The data is further reduced by calculating the initial ($R_i$) and final ($R_f$) ratios. These are the average ratio values during part or all of the pre-stimulation period, and during sample points during the stimulation period. The response to the stimulus $\rho = R_f/R_i$ is then calculated.

Control responses are obtained by performing assays in the presence of a compound with the desired properties (positive control) and in the absence of pharmacological agents (negative control). Responses to the negative (N) and positive (P) controls are calculated as above. The activity A of the assay well relative to positive and negative controls is defined as:

$$A = \frac{N-R}{N-P}.$$

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), CaCl$_2$ (1.26), KCl (5.33), KH$_2$PO$_4$ (0.44), MgCl$_2$ (0.5), MgSO$_4$ (0.41), NaHCO$_3$ (4), Na$_2$HPO$_4$ (0.3), glucose (5.6), HEPES (10), CdCl$_2$ (0.4), NiCl$_2$ (0.1), TTX (0.25×10$^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM): 150 K-gluconate, 10 NaCl, 0.1 EGTA, 10 Hepes, 2 MgCl$_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

The exemplified compounds of Table 1 herein are active against one or more sodium channels as measured using the assays described hereinabove.

The compounds of the present invention exhibited activity against NaV 1.3 channel.

The activity of selected compounds of the present invention against NaV 1.3 channel is shown below in Table 3. In Table 3, the letter designations have the following meaning: "A" means<2 μM; "B" means between 2 μM and 10 μM; "C" means between 10 μM and 20 μM; "D" means>20 μM.

TABLE 3

| Cmpd. No. | IC$_{50}$ |
|---|---|
| 1 | D |
| 2 | B |
| 3 | C |
| 4 | C |
| 5 | D |
| 6 | C |
| 7 | C |
| 8 | D |
| 9 | C |

The compounds of the present invention exhibited activity against NaV 1.7 channel.

The activity of selected compounds of the present invention against NaV 1.7 channel is shown below in Table 4. In Table 4, the letter designations have the following meaning: "A" means<2 μM; "B" means between 2 μM and 10 μM; "C" means between 10 μM and 20 μM; "D" means>20 μM.

TABLE 4

| Cmpd. No. | IC$_{50}$ |
|---|---|
| 1 | D |
| 2 | B |
| 3 | B |
| 4 | D |
| 5 | D |
| 6 | D |
| 7 | C |
| 8 | D |
| 9 | C |

The compounds of the present invention exhibited activity against NaV 1.8 channel.

The activity of selected compounds of the present invention against NaV 1.8 channel is shown below in Table 5. In Table 5, the letter designations have the following meaning: "A" means<2 μM; "B" means between 2 μM and 10 μM; "C" means between 10 μM and 20 μM; "D" means>20 μM.

TABLE 5

| Cmpd. No. | IC$_{50}$ |
|---|---|
| 1 | A |
| 2 | A |
| 3 | A |
| 4 | A |
| 5 | B |
| 6 | B |
| 7 | A |
| 8 | B |
| 9 | B |

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:
1. A compound of formula I:

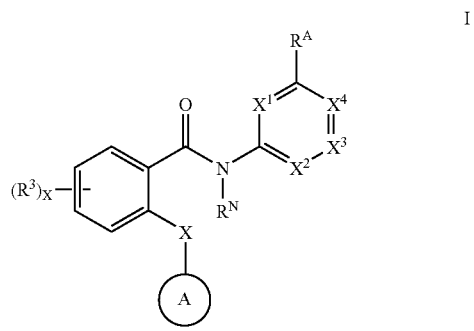

or a pharmaceutically acceptable salt thereof, wherein:
X is O, s, NR$^N$, c(0), or C(R$^N$)$_2$;
Ring A is phenyl or a 5-7 membered heteroaryl ring, wherein ring A is optionally substituted with up to y occurrences of R$^5$;
X$^1$, X$^2$, X$^3$ and X$^4$ are each independently nitrogen or C—R$^4$ provided that at least one of X$^1$, X$^2$, X$^3$ and X$^4$ is nitrogen and provided that X$^1$, X$^2$, X$^3$ and X$^4$ are not all simultaneously nitrogen;
R$^A$ is selected from SO$_2$N(R$^2$)$_2$, SO$_2$R$^1$, NR$^2$SO$_2$R$^1$;
R$^1$ is C$_{1-6}$ aliphatic, wherein up to two carbon atoms other than the atom attached to the nitrogen or oxygen atom is optionally replaced with 0, S, NR$^N$, or C(O);
each R$^2$ is independently hydrogen, or C$_{1-6}$ aliphatic, wherein up to two carbon atoms other than the atom attached to the nitrogen or oxygen atom is optionally replaced with O, S, NR$^N$, or C(O);
x is 0-4;
y is 0-4;
each occurrence of R$^N$ is independently selected from hydrogen or a C$_{1-6}$ aliphatic group optionally substituted with 1-3 independent occurrences of —R$^J$, oxo, thioxo, —CO$_2$R$^J$, —OR$^J$, —N(R$^J$)$_2$, —SR$^J$, —NO$_2$, halogen, —CN, —C$_{1-4}$haloalkyl, —C$_{1-4}$haloalkoxy, —C(O)N(R$^J$)$_2$, —NR$^J$C(O)R$^J$, —SO$_2$R$^J$, —SO$_2$N(R$^J$)$_2$, —NR$^J$SO$_2$R$^J$, —NR$^J$CON(R$^J$)$_2$, —NR$^J$CO$_2$R$^J$, —COR$^J$, —OCOR$^J$, —OCON(R$^J$)$_2$, —SOR$^J$, —NR$^J$SO$_2$N(R$^J$)$_2$, —COCOR$^J$, —COCH$_2$COR$^J$, —OP(O)(OR$^J$)$_2$, —P(O)(OR$^J$)$_2$, —PO(OR$^J$)(R$^J$), —P(O)(R$^J$)$_2$, or —OP(O)(R$^J$)$_2$; wherein
R$^J$ is hydrogen or unsubstituted C$_{1-6}$ aliphatic;
each occurrence of R$^3$, R$^4$, and R$^5$ is independently Q-R$^X$;
Q is a bond or is a C$_{1-6}$ aliphatic chain wherein up to three methylene units of Q are optionally and independently replaced by —NH—, —NR—, —O—, —S—, —CO$_2$—, —OC(O)—, —C(O)CO—, —C(O)—, —C(S)—, —C(O)NH—, —C(O)NR—, —C(=N—CN)—, —NHCO—, —NRCO—, —NHC(O)O—, —NRC(O)O—, —SO$_2$NH—, —SO$_2$NR—, —NHSO$_2$—, —NRSO$_2$—, —NHC(O)NH—, —NRC(O)NH—, —NRC(O)NR—, —NHC(O)NR, —OC(O)NH—, —OC(O)NR—, —NHSO$_2$NH—, —NRSO₂NH—, —NHSO₂NR—, —NRSO₂NR—, —SO— or —SO₂—; wherein Q is optionally substituted with 1-3 independent occurrences of $R^Q$;

each occurrence of $R^X$ is independently selected from —R', halogen, —NO₂, —CN, —OR', —SR', —N(R')₂, —NR'C(O)R', —NR'C(O)N(R')₂, —NR'CO₂R', —C(O)R', —CO₂R', —OC(O)R', —C(O)N(R')₂, —OC(O)N(R')₂, —SOR', —SO₂R', —SO₂N(R')₂, —NR'SO₂R', —NR'SO₂N(R')₂, —C(O)C(O)R', —C(O)CH₂C(O)R', —OP(O)(OR')₂, —P(O)(OR')₂, —PO(OR')(R'), —P(O)(R')₂, or —OP(O)(R')₂;

each occurrence of R is independently selected from hydrogen or a $C_{1-6}$ aliphatic group optionally substituted with 1-3 independent occurrences of —$R^T$, -T-Ar¹, halogen, oxo, thioxo, —$OR^T$, —$SR^T$, —$N(R^T)_2$, —NO₂, —$C_{1-4}$haloalkyl, —$C_{1-4}$haloalkoxy, —CN, —$CO_2R^T$, —$COR^T$, —$CON(R^T)_2$, —$OCOR^T$, —$NR^TCOR^T$, —$SO_2R^T$, —$SO_2N(R^T)_2$, or —$NR^TSO_2R^T$; wherein each $R^T$ is independently hydrogen or unsubstituted $C_{1-6}$ aliphatic; or any two $R^T$ groups, on the same substituent or different substituents, together with the atom(s) to which each group is bound, optionally form a 3-8 membered saturated or partially unsaturated monocyclic ring, or a 5-6 membered monocyclic aryl ring having 0-3 heteroatoms independently selected from nitrogen, oxygen, or sulfur; wherein said monocyclic ring is optionally substituted with 1-3 independent occurrences of —$R^R$, -T-Ar¹, halogen, oxo, thioxo, —$OR^R$, —$SR^R$, —$N(R^R)_2$, —NO₂, —$C_{1-4}$haloalkyl, —$C_{1-4}$haloalkoxy, —CN, —$CO_2R^R$, —$COR^R$, —$CON(R^R)_2$, —$OCOR^R$, —$NR^RCOR^R$, —$SO_2R^R$, —$SO_2N(R^R)_2$, or —$NR^RSO_2R^R$; wherein each $R^R$ is independently hydrogen or unsubstituted $C_{1-6}$ aliphatic;

T is $(CH_2)_w$;

w is 0-2;

Ar¹ is selected from a 3-8 membered saturated or partially unsaturated ring, a 5-6 membered aryl ring, a 3-7 membered heterocyclic ring having 1-3 heteroatoms independently selected from nitrogen, oxygen, or sulfur, a 5-6 membered heteroaryl ring having 1-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein Ar¹ is optionally substituted with 1-3 independent occurrences of —$R^W$, oxo, thioxo, —$CO_2R^W$, —$OR^W$, —$N(R^W)_2$, —$SR^W$, —NO₂, halogen, —CN, —$C_{1-4}$haloalkyl, —$C_{1-4}$haloalkoxy, —$C(O)N(R^W)_2$, —$NR^WC(O)R^W$, —$SO_2R^W$, —$SO_2N(R^W)_2$, —$NR^WSO_2R^W$, —$NR^WCON(R^W)_2$, —$NR^WCO_2R^W$, —$COR^W$, —$OCOR^W$, —$OCON(R^W)_2$, —$SOR^W$, —$NR^WSO_2N(R^W)_2$, —$COCOR^W$, —$COCH_2COR^W$, —$OP(O)(OR^W)_2$, —$P(O)(OR^W)_2$, —$PO(OR^W)(R^W)$, —$P(O)(R^W)_2$, or —$OP(O)(R^W)_2$; wherein $R^W$ is hydrogen or unsubstituted $C_{1-6}$ aliphatic;

$R^Q$ is selected from halogen, —$R^S$, —$N(R^S)_2$, —$SR^S$, —$OR^S$, $C_{3-10}$ cycloaliphatic, $C_{6-10}$ aryl, 5-10 membered heteroaryl, 5-10 membered heterocyclyl, oxo, thioxo, —$C_{1-4}$haloalkoxy, —$C_{1-4}$haloalkyl, —NO₂, —CN, —CF₃, —OCF₃, —$CO_2R^S$, —$COR^S$, —$OC(O)R^S$ or —$NR^SC(O)R^S$; wherein $R^S$ is hydrogen or unsubstituted $C_{1-6}$ aliphatic; or any two $R^Q$ or two $R^S$ groups, or any combination of an $R^Q$ group with an $R^S$ group on the same substituent or different substituents, together with the atom(s) to which each group is bound, optionally form a 3-8 membered saturated or partially unsaturated monocyclic ring, or a 5-6 membered monocyclic aryl ring; each ring having 0-3 heteroatoms independently selected from nitrogen, oxygen, or sulfur; wherein any of said monocyclic ring is optionally substituted with 1-3 independent occurrences of $R^O$, halogen, oxo, thioxo, —$OR^O$, —$SR^O$, —$N(R^O)_2$, —NO₂, —$C_{1-4}$haloalkyl, —$C_{1-4}$haloalkoxy, —CN, —$CO_2R^O$, —$COR^O$, —$CON(R^O)_2$, —$OCOR^O$, —$NR^OCOR^O$, —$SO_2R^O$, —$SO_2N(R^O)_2$, or —$NR^OSO_2R^O$; wherein $R^O$ is hydrogen or unsubstituted $C_{1-6}$ aliphatic; and each occurrence of R' is independently selected from hydrogen or a $C_{1-8}$ aliphatic, $C_{6-10}$ aryl, a heteroaryl ring having 5-10 ring atoms, or a heterocyclyl ring having 3-10 ring atoms, or wherein R and R' taken together with the atom(s) to which they are bound, or two occurrences of R' taken together with the atom(s) to which they are bound, form a 5-8 membered cycloalkyl, heterocyclyl, aryl, or heteroaryl ring having 0-3 heteroatoms independently selected from nitrogen, oxygen, or sulfur; wherein said $C_{1-8}$ aliphatic, $C_{6-10}$ aryl, heteroaryl ring or heterocyclyl ring is optionally substituted with 1-3 independent occurrences of $R^I$, halogen, oxo, thioxo, —$OR^I$, —$SR^I$, —$N(R^I)_2$, —NO₂, —$C_{1-4}$haloalkyl, —$C_{1-4}$haloalkoxy, —CN, —$CO_2R^I$, —$COR^I$, —$CONHR^I$, —$OCOR^I$, —$NR^ICOR^I$, —$SO_2R^I$, —$SO_2N(R^I)_2$, or —$NR^ISO_2R^I$; wherein $R^I$ is hydrogen or unsubstituted $C_{1-6}$ aliphatic.

2. The compound according to claim 1, wherein ring A is optionally substituted phenyl.

3. The compound according to claim 1, wherein ring A is an optionally substituted 5-7 membered heteroaryl ring.

4. The compound according to claim 3, wherein ring A is selected from:

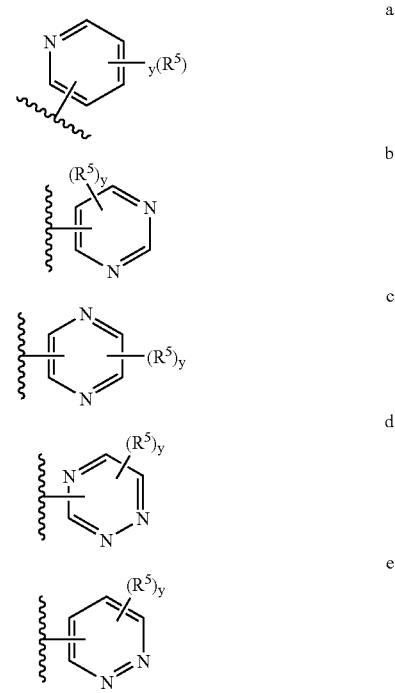

-continued

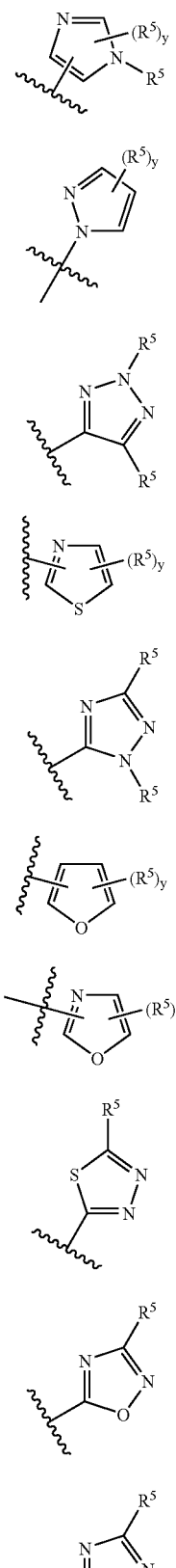

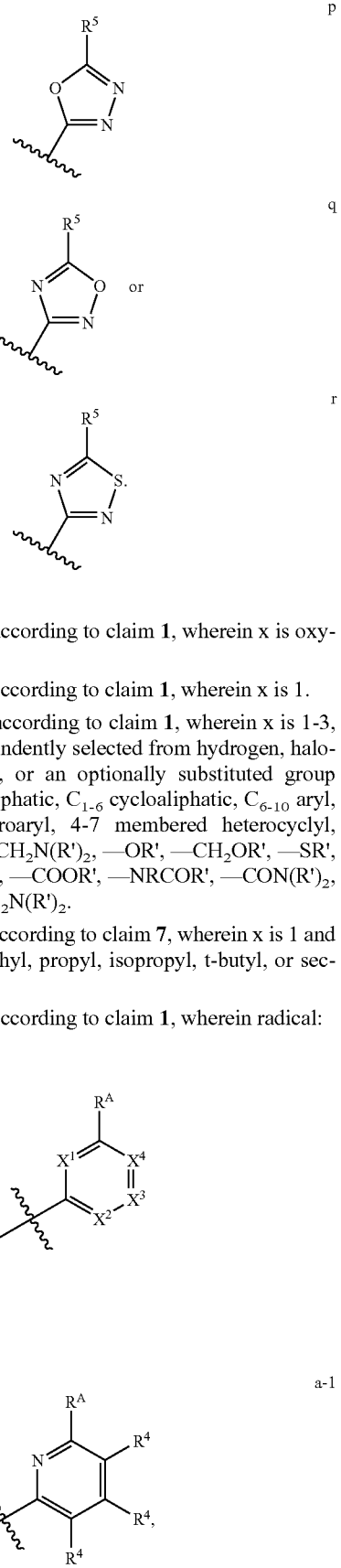

5. The compound according to claim 1, wherein x is oxygen.

6. The compound according to claim 1, wherein x is 1.

7. The compound according to claim 1, wherein x is 1-3, and each $R^3$ is independently selected from hydrogen, halogen, CN, $CF_3$, $NO_2$, or an optionally substituted group selected from $C_{1-6}$ aliphatic, $C_{1-6}$ cycloaliphatic, $C_{6-10}$ aryl, 5-6 membered heteroaryl, 4-7 membered heterocyclyl, aralkyl, —N(R')$_2$, —CH$_2$N(R')$_2$, —OR', —CH$_2$OR', —SR', —CH$_2$SR', —C(O)R', —COOR', —NRCOR', —CON(R')$_2$, —S(O)$_2$R', or —S(O)$_2$N(R')$_2$.

8. The compound according to claim 7, wherein x is 1 and $R^3$ is $CF_3$, methyl, ethyl, propyl, isopropyl, t-butyl, or sec-butyl.

9. The compound according to claim 1, wherein radical:

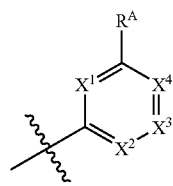

is selected from:

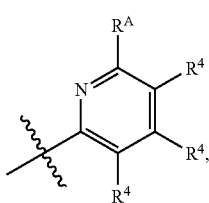

a-1

-continued a-2 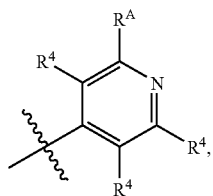

a-3 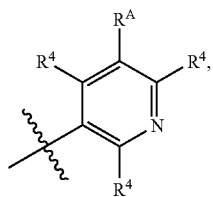

b-1 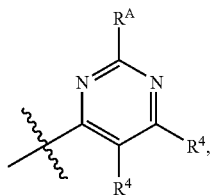

b-2 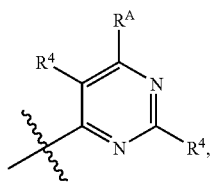

c-1 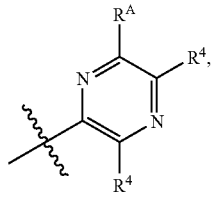

d-1 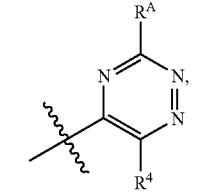

e-1 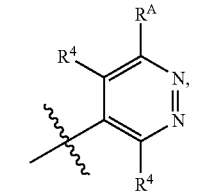

e-2 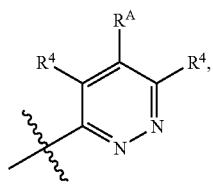

-continued d-2 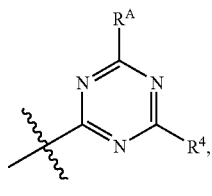

d-3 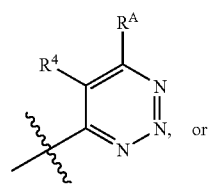, or d-4 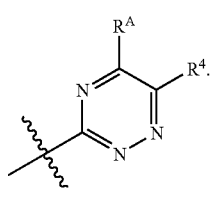

10. The compound according to claim 9, wherein radical

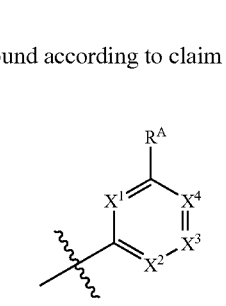

is selected from ring a-1, a-2 or a-3.

11. The compound according to claim 10, wherein each $R^4$ is hydrogen.

12. The compound according to claim 1, wherein $R^4$ is selected from $SO_2N(R^2)_2$ or $SO_2R^1$.

13. The compound according to claim 12, wherein $R^4$ is $SO_2N(R^2)_2$ and both $R^2$ are hydrogen.

14. The compound according to claim 12, wherein $R^4$ is $SO_2R^1$ and $R^1$ is $C_{1-6}$ alkyl.

15. The compound according to claim 1, wherein y is 1-3, and each $R^5$ is independently selected from halogen or an optionally substituted $C_{1-4}$ aliphatic group.

16. The compound according to claim 1, wherein said compound has the structure of formula III-A, III-B or III-C:

III-A

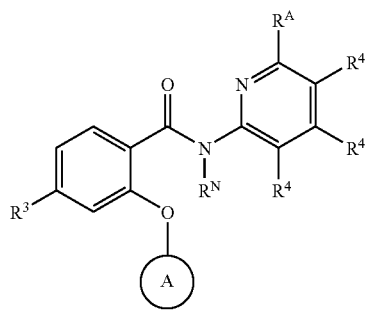

-continued
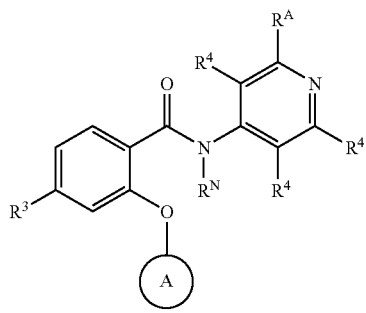
III-B
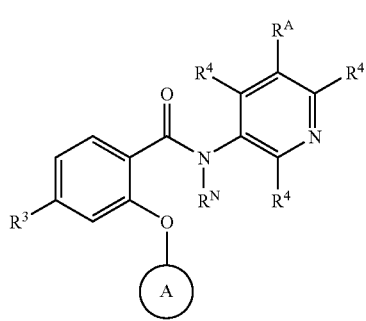
III-C
or a pharmaceutically acceptable salt thereof, wherein Ring A, $R^3$, $R^5$, $R^N$, $R^A$ and $R^4$ are defined in claim 1.
17. A compound selected from:
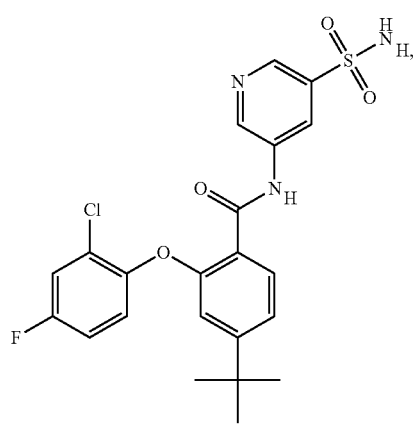
-continued
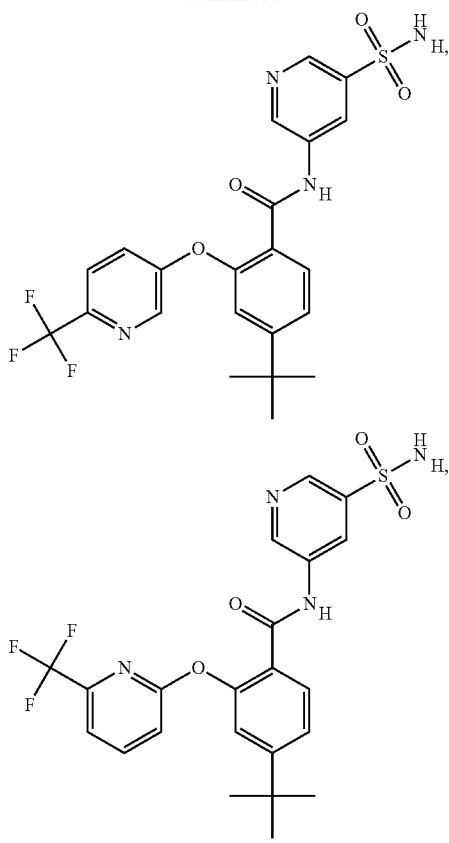
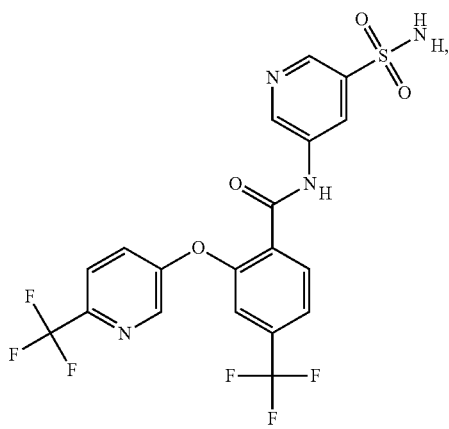
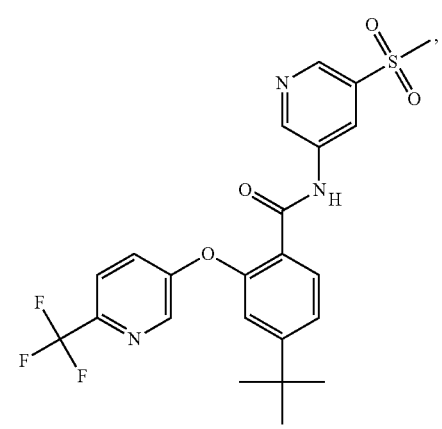

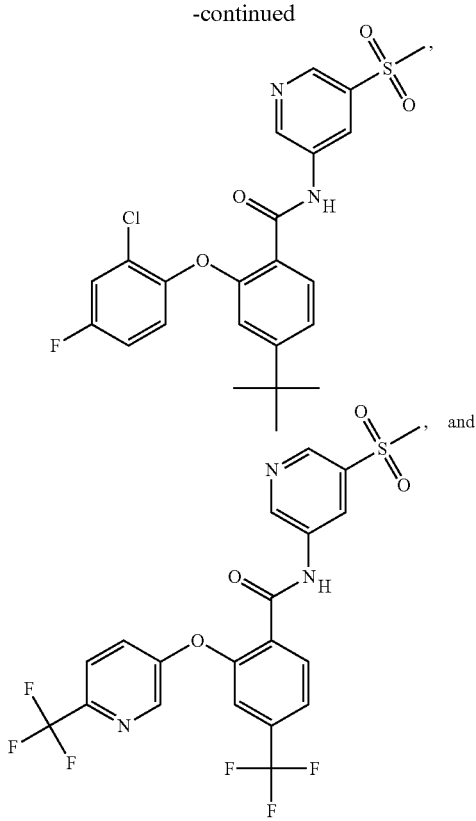
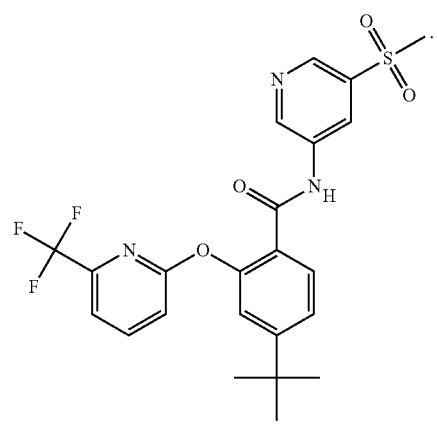
18. A pharmaceutical composition comprising a compound of claim 1, and a pharmaceutically acceptable carrier, adjuvant, or vehicle.
* * * * *